United States Patent [19]

Jaunin

[11] 3,996,374
[45] Dec. 7, 1976

[54] ISOINDOLE DERIVATIVES AS APPETITE SUPPRESSANTS

[75] Inventor: Roland Jaunin, Basel, Switzerland

[73] Assignee: Hoffmann-La Roche Inc., Nutley, N.J.

[22] Filed: Nov. 20, 1975

[21] Appl. No.: 633,514

[30] Foreign Application Priority Data

Nov. 28, 1974  Switzerland ............... 15795/74
Sept. 23, 1975  Switzerland ............... 12342/75

[52] U.S. Cl. .................. 424/274; 260/247.2 A; 260/247.2 B; 260/268 BC; 260/293.61; 260/307.1 A; 260/309.7; 260/310 D; 260/468 K; 260/558 R; 260/326.1; 424/248; 424/250; 424/267; 424/272; 424/273

[51] Int. Cl.² ............... C07D 209/44; A61K 31/40

[58] Field of Search ............... 260/326.1, 247.2 A, 260/247.2 B, 268 BC, 293.61, 307 FA, 309.7, 310 D; 424/274

[56] References Cited
UNITED STATES PATENTS 3,466,298  9/1969  Sulkowski et al. ........... 260/326.1
3,558,649  1/1971  Metlesics et al. ........... 260/326.1
3,879,415  4/1975  Metlesics et al. ........... 260/326.1

OTHER PUBLICATIONS

Fryer et al., "J. Org. Chem.," vol. 34 (3), pp. 649–654 (1969).
Fryer, "J. Het. Chem.," vol. 9(4), pp. 747–758 (1972).

Primary Examiner—Lewis Gotts
Assistant Examiner—S. P. Williams
Attorney, Agent, or Firm—Samuel L. Welt; Bernard S. Leon; William G. Isgro

[57] ABSTRACT

Isoindole derivatives of the formula

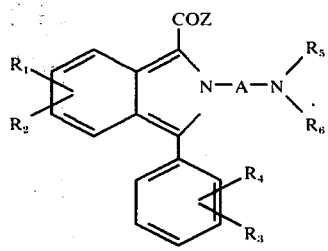

wherein $R_1$–$R_6$, A and Z are as hereinafter described. The isoindole derivatives are useful as appetite suppressants.

38 Claims, No Drawings

ISOINDOLE DERIVATIVES AS APPETITE SUPPRESSANTS

BRIEF SUMMARY OF THE INVENTION

The invention relates to isoindole derivatives of the formula

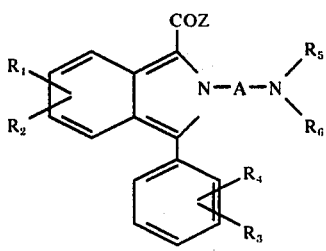

wherein A is alkylene containing 2–10 carbon atoms, Z is the group —OR or

R is alkyl, cycloalkyl, cycloalkylalkyl, alkoxyalkyl, allyl or aralkyl, $R_1$, $R_2$, $R_3$ and $R_4$, independently, are hydrogen, halogen, alkyl, alkoxy or trifluoromethyl, and $R_5$ and $R_6$, independently, are hydrogen, alkyl cycloalkyl, cycloalkylalkyl, hydroxyalkyl, alkoxyalkyl, aryl or aralkyl, or $R_5$ and $R_6$ taken together, are the group —$(CH_2)_n$—, wherein n is an integer of 2–7, or $R_5$ and $R_6$, taken together with the nitrogen atom to which they are attached are a 5-membered or 6-membered heterocyclic ring containing an oxygen atom or an additional nitrogen atom which may be substituted by alkyl or hydroxyalkyl, and $R_7$ and $R_8$, independently, are hydrogen alkyl, cycloalkyl, cycloalkylalkyl, alkoxyalkyl or aralkyl, provided that at least one of $R_7$ and $R_8$ is other than hydrogen, or a pharamaceutically acceptable acid addition salt thereof.

DETAILED DESCRIPTION OF THE INVENTION

As used herein, the term "alkyl", alone or in combination, for example, with "alkoxy", denotes a straight-chain or branched-chain saturated hydrocarbon group containing up to 6 carbon atoms, for example, methyl, ethyl, propyl, isopropyl, butyl, and the like. The term "lower alkoxy" denotes an alkyl ether group in which the lower alkyl is as described above. The term "alkylene" denotes a straight-chain or branched-chain alkylene, for example, ethylene, methylethylene, trimethylene, tetramethylene, and the like. The term "cycloalkyl", alone or in combination, denotes $C_3$–$C_6$ cycloalkyl, i.e., cyclopropyl, cyclobutyl, cyclopentyl and cyclohexyl. The 5-membered or 6-membered heterocyclic ring is derived from a saturated heterocyclic compound comprising two nitrogen atoms or one nitrogen atom and one oxygen atom where the second nitrogen atom may be substituted by alkyl or hydroxyalkyl, for example, morpholino, N-methyl-piperazino, piperazino, and the like. The term "halogen" denotes fluorine, chlorine, bromine and iodine. The term "aryl" denotes mononuclear or polynuclear aromatic groups in which one or more hydrogen atoms may be replaced by alkyl, alkoxy or halogen, for example, phenyl, halophenyl, methoxyphenyl and the like. The term "leaving atom or group" comprises halogen, arylsulfonyloxy, such as tosyloxy and alkylsulfonyloxy, such as mesyloxy. The term "protecting group" comprises acyl, for example, alkanoyl such as acetyl, or the like, carbalkoxy such as carbomethoxy, or the like, carbophenylalkoxy such as carbobenzoxy, or the like, and benzyl.

The compounds of the invention are isoindole derivatives characterized by the formula

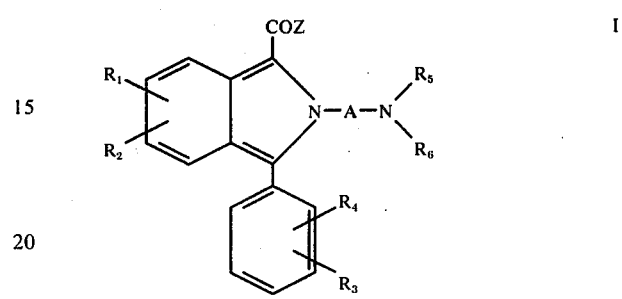

wherein A is alkylene containing 2–10 carbon atoms, Z is the group —OR or

R is alkyl, cycloalkyl, cycloalkylalkyl, alkoxyalkyl, allyl or aralkyl, $R_1$, $R_2$, $R_3$ and $R_4$, independently, are hydrogen, halogen, alkyl, alkoxy or trifluoromethyl, and $R_5$ and $R_6$, independently, are hydrogen, alkyl, cycloalkyl, cycloalkylalkyl, hydroxyalkyl, alkoxyalkyl, aryl or aralkyl, or $R_5$ and $R_6$, taken together, are the group —$(CH_2)_n$—, wherein n is an integer of 2–7, or $R_5$ and $R_6$, taken together with the nitrogen atom to which they are attached, are a 5-membered or 6-membered heterocyclic ring containing an oxygen atom or an additional nitrogen atom which may be substituted by alkyl or hydroxyalkyl, and $R_7$ and $R_8$, independently, are hydrogen or alkyl, cycloalkyl, cycloalkylalkyl, alkoxyalkyl or aralkyl, provided that at least one of $R_7$ and $R_8$ is other than hydrogen, or a pharmaceutically acceptable acid addition salt thereof.

In a preferred embodiment of the compounds of formula I of the invention, $R_1$, $R_2$, $R_3$ and $R_4$ each, independently, is hydrogen, halogen, or trifluoromethyl. In a more preferred embodiment, $R_4$ is hydrogen and $R_1$ is chlorine, fluorine or trifluoromethyl. In a still more preferred embodiment, $R_2$ and $R_3$ each is hydrogen, chlorine or fluorine. Furthermore, compounds of formula I, wherein $R_5$ and $R_6$ each, independently, is alkyl, especially ethyl or isopropyl are preferred. In yet another preferred embodiment, A is ethylene or trimethylene. Preferred compounds of formula I are also those wherein Z is the group —OR or —$NHR_7$, wherein R and $R_7$ preferably are alkyl, especially ethyl or isopropyl.

As will be evident from the foregoing, especially preferred compounds of formula I are those wherein $R_4$ is hydrogen, $R_1$ is chlorine, fluorine, or trifluoromethyl, $R_2$ and $R_3$ each, independently, is hydrogen, chlorine or fluorine, $R_5$ and $R_6$ each, independently, is ethyl or isopropyl, A is ethylene or trimethylene, Z is the group —OR or —$NHR_7$ and R and $R_7$ are ethyl or isopropyl.

Especially preferred compounds of formula I are:
5-chloro-2-[2-(diethylamino)ethyl]-3-phenylisoindole-1-carboxylic acid ethyl ester,
5-chloro-2-[3-(diethylamino)propyl]-3-phenylisoindole-1-carboxylic acid ethyl ester,
5-chloro-3-(p-chlorophenyl)-2-[2-(diethylamino)ethyl]-isoindole-1-carboxylic acid ethyl ester,
5,7-dichloro-2-[2-(diethylamino)ethyl]-3-phenylisoindole-1-carboxylic acid ethyl ester and
5-chloro-2-[2-(diethylamino)ethyl]-3-phenylisoindole-1-carboxylic acid ethyl amide.

Other preferred compounds of formula I are:
5-chloro-2-[2-(dibutylamino)ethyl]-3-phenylisoindole-1-carboxylic acid ethyl ester,
5-chloro-2-[2-(diethylamino)ethyl]-3-phenylisoindole-1-carboxylic acid benzyl ester,
5-chloro-2-[2-(diethylamino)ethyl]-3-phenylisoindole-1-carboxylic acid isobutyl ester,
5-chloro-2-[2-(diethylamino)ethyl]-3-phenylisoindole-1-carboxylic acid allyl ester,
5-chloro-2-[2-(diisopropylamino)ethyl]-3-phenylisoindole-1-carboxylic acid ethyl ester,
5-chloro-2-[2-(diethylamino)ethyl]-3-phenylisoindole-1-carboxylic acid isopropyl ester,
6-chloro-2-[2-(diethylamino)ethyl]-3-phenylisoindole-1-carboxylic acid ethyl ester,
5-chloro-2-[2-(diethylamino)ethyl]-3-(o-fluorophenyl)-isoindole-1-carboxylic acid ethyl ester,
3-(p-chlorophenyl)-2-[2-(diethylamino)ethyl]-isoindole-1-carboxylic acid ethyl ester,
5-chloro-2-[2-(diethylamino)ethyl]-3-phenylisoindole-1-carboxylic acid methyl amide,
2-[3-(butylmethylamino)propyl]-5-chloro-3-phenylisoindole-1-carboxylic acid ethyl ester,
2-{3-[bis(2-hydroxyethyl)amino]propyl}-5-chloro-3-phenylisoindole-1-carboxylic acid ethyl ester,
5-chloro-2-[2-(diethylamino)ethyl]-3-phenylisoindole-1-carboxylic acid dimethyl amide,
5-chloro-3-(3,4-dichlorophenyl)-2-[2-(diethylamino)ethyl]-isoindole-1-carboxylic acid ethyl ester,
2-[2-(diethylamino)ethyl]-3-phenyl-5-trifluoromethyl-isoindole-1-carboxylic acid ethyl ester,
2-[5-(butylmethylamino)-3,3-dimethylpentyl]-5-chloro-3-phenylisoindole-1-carboxylic acid ethyl ester,
5-chloro-2-[4-(isopropylamino)pentyl]-3-phenylisoindole-1-carboxylic acid ethyl ester,
5-chloro-2-{3-[bis(methoxyethyl)amino]propyl}-3-phenylisoindole-1-carboxylic acid ethyl ester,
2-[3-(cyclohexylamino)propyl]-5-chloro-3-phenylisoindole-1-carboxylic acid ethyl ester and
5-chloro-2-[3-(N-methylanilino)propyl]-3-phenylisoindole-1-carboxylic acid ethyl ester.

According to the process of the invention, the isoindole derivatives, that is, the compounds of formula I and pharmaceutically acceptable acid addition salts thereof are prepared by a. reductively aminating a compound of the formula

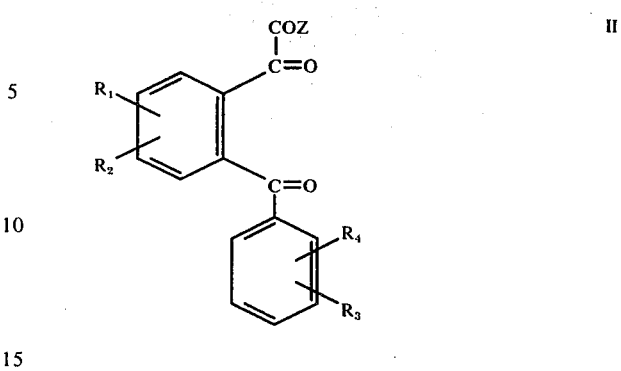

wherein Z, $R_1$, $R_2$, $R_3$ and $R_4$ are as previously described, with a diamine of the formula $$H_2N-A-N\diagdown_{R_6}^{R_5} \qquad III$$

wherein A, $R_5$ and $R_6$ are as previously described, or b. reacting a compound of the formula ![Formula IV structure]

wherein A, Z, $R_1$, $R_2$, $R_3$ and $R_4$ are as previously described and X is a leaving atom or group, with an amine of the formula $$HN\diagdown_{R_6}^{R_5} \qquad V$$

wherein $R_5$ and $R_6$ are as previously described, or c. to prepare a compound of formula I wherein $R_5$ and $R_6$, independently, are alkyl, cycloalkyl, cycloalkylalkyl, alkoxyalkyl, aryl or aralkyl or $R_5$ and $R_6$, taken together are the group $-(CH_2)_n-$, wherein $n$ is an integer of 2–7, or $R_5$ and $R_6$ taken together with the nitrogen atom to which they are attached are a 5-membered or 6-membered heterocyclic ring containing an oxygen atom or an additional nitrogen atom which is substituted by alkyl, and A, Z, $R_1$, $R_2$, $R_3$ and $R_4$ are as previously described, reacting a compound of the formula

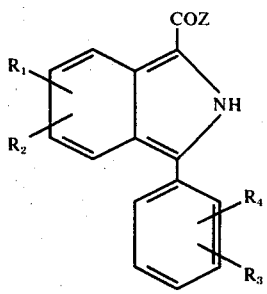

wherein Z, $R_1$, $R_2$, $R_3$ and $R_4$ are as previously described, with a compound of the formula

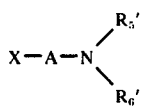   VII wherein A and X are as previously described and $R'_5$ and $R'_6$, independently, are alkyl, cycloalkyl, cycloalkylalkyl, alkoxyalkyl, aryl or aralkyl or $R'_5$ and $R'_6$, taken together, are the group $-(CH_2)_n-$, wherein n is an integer of 2–7, or $R'_5$ and $R'_6$, taken together with the nitrogen atom to which they are attached are a 5-membered or 6-membered heterocyclic ring containing an oxygen atom or an additional nitrogen atom which is substituted with alkyl, or d. to prepare a compound of formula I wherein Z is the group —OR, wherein R is alkyl, cycloalkyl, cycloalkylalkyl, alkoxyalkyl or aralkyl, and $R_5$ and $R_6$, independently, are alkyl, cycloalkyl, cycloalkylalkyl, alkoxyalkyl, aryl or aralkyl, or $R_5$ and $R_6$, taken together are the group $-(CH_2)_n-$, wherein n is an integer of 2–7, or $R_5$ and $R_6$, taken together with the nitrogen atom to which they are attached are a 5-membered or 6-membered heterocyclic ring containing an oxygen atom or an additional nitrogen atom which is substituted with alkyl, and A, $R_1$, $R_2$, $R_3$ and $R_4$ are as previously described, reducing a compound of the formula

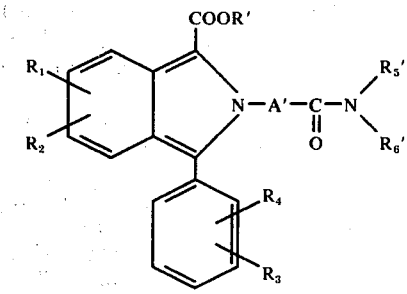   VIII wherein $R_1$, $R_2$, $R_3$, $R_4$, $R'_5$ and $R'_6$ are as previously described, A' is alkylene containing 1–9 carbon atoms and R' is alkyl, cycloalkyl, cycloalkylalkyl, alkoxyalkyl or aralkyl, with an electrophilic hydride reducing agent, or e. to prepare a compound of formula I wherein Z is the group —OR, wherein R is alkyl, cycloalkyl, cycloalkylalkyl, alkoxyalkyl or aralkyl, $R_5$ and $R_6$, independently, are alkyl, cycloalkyl, cycloalkylalkyl, alkoxyalkyl, aryl, or aralkyl or $R_5$ and $R_6$, taken together are the group $-(CH_2)_n-$, wherein n is an integer of 2–7, or $R_5$ and $R_6$, taken together with the nitrogen atom to which they are attached, are a 5-membered or 6-membered heterocyclic ring containing an oxygen atom or an additional nitrogen atom which is substituted with alkyl, and A, $R_1$, $R_2$, $R_3$ and $R_4$ are as previously described, reacting a benzodiazepine derivative of the formula

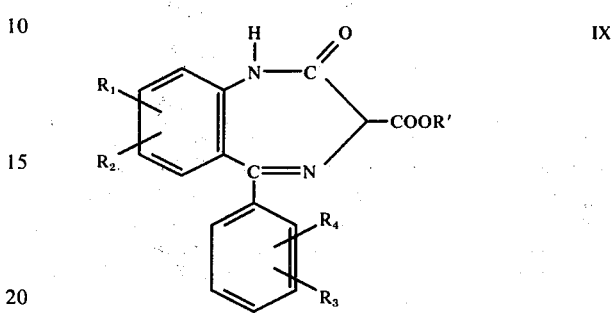   IX wherein R', $R_1$, $R_2$, $R_3$ and $R_4$ are as previously described, with a strong base and a compound of formula VII, or f. to prepare a compound of formula I wherein Z is the group —OR, wherein R is alkyl, cycloalkyl, cycloalkylalkyl, alkoxyalkyl or aralkyl, $R_5$ is hydrogen and $R_6$ is hydrogen, alkyl, cycloalkyl, cycloalkylalkyl, alkoxyalkyl or aralkyl, and A, $R_1$, $R_2$, $R_3$ and $R_4$ are as previously described, reductively aminating a compound of the formula

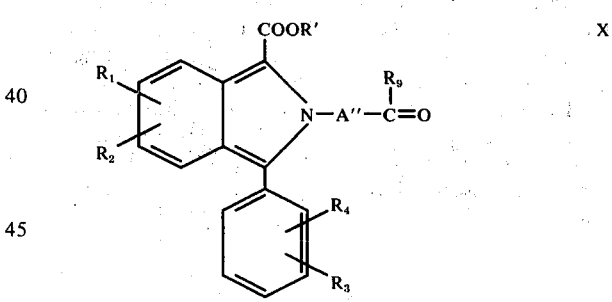   X wherein $R_9$ is hydrogen or alkyl and A" is alkylene containing 1–9 carbon atoms, provided that A" and $R_9$ together contain at most 9 carbon atoms, and R', $R_1$, $R_2$, $R_3$ and $R_4$ are as previously described, with an amine of formula V wherein $R_5$ is hydrogen and $R_6$ is hydrogen, alkyl, cycloalkyl, cycloalkylalkyl, alkoxyalkyl or aralkyl, or g. to prepare a compound of formula I wherein $R_5$ and $R_6$, independently, are hydrogen, alkyl, cycloalkyl, cycloalkylalkyl, hydroxyalkyl, alkoxyalkyl or aralkyl, provided that at least one of $R_5$ and $R_6$ is other than hydrogen, and A, Z, $R_1$, $R_2$, $R_3$ and $R_4$ are as previously described, appropriately monosubstituting or disubstituting the primary amino group on the nitrogen atom in a compound of the formula

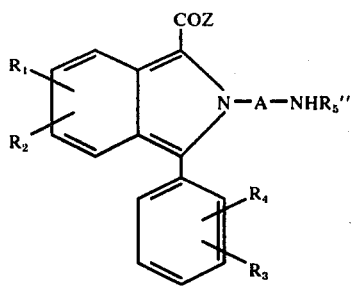

Ia wherein A, Z, $R_1$, $R_2$, $R_3$ and $R_4$ are as previously described and $R''_5$ is hydrogen, alkyl, cycloalkyl, cycloalkylalkyl, hydroxyalkyl alkoxyalkyl or aralkyl, or h. to prepare a compound of formula I wherein $R_5$ is hydrogen and A, Z, $R_1$, $R_2$, $R_3$, $R_4$ and $R_6$ are as previously described, cleaving the protecting group which is present in a compound of the formula

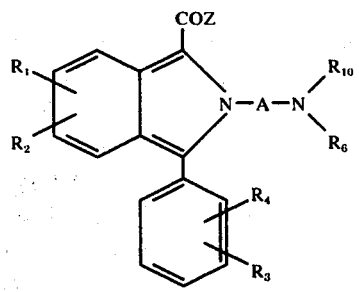

XI wherein A, Z, $R_1$, $R_2$, $R_3$, $R_4$ and $R_6$ are as previously described, and $R_{10}$ is a protecting group, i. to prepare a compound of formula I wherein Z is the group —OR, wherein R is alkyl, cycloalkyl, cycloalkylalkyl, alkoxyalkyl or aralkyl, $R_5$ is hydrogen, alkyl, cycloalkyl, cycloalkylalkyl, alkoxyalkyl, aryl or aralkyl and $R_6$ is alkyl, cycloalkylalkyl, alkoxyalkyl or aralkyl, wherein said alkyl and alkoxyalkyl contain at least 2 carbon atoms, and A, $R_1$, $R_2$, $R_3$ and $R_4$ are as previously described, reducing a compound of the formula

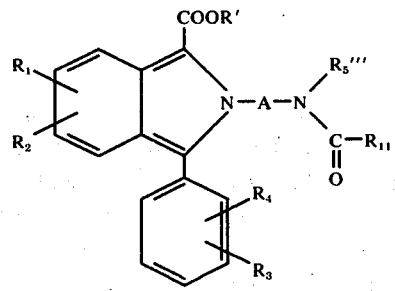

XII wherein A, $R_1$, $R_2$, $R_3$, $R_4$ and R' are as previously described, $R'''_5$ is hydrogen, alkyl, cycloalkyl, cycloalkylalkyl, alkoxyalkyl, aryl or aralkyl and $R_{11}$ is alkyl, cycloalkyl, cycloalkylalkyl, alkoxyalkyl, aryl or aralkyl and wherein the alkyl groups each contain a maximum of 5 carbon atoms, with an electrophilic hydride reducing agent, and j. if desired, converting a compound of formula I obtained into a pharmaceutically acceptable acid addition salt.

The reductive amination of a compound of formula II with a diamine of formula III in accordance with process embodiment (a) is carried out according to a variety of known methods by reacting a compound of formula II with a diamine of formula III in the presence of a suitable reducing agent. Thus, the reductive amination can be carried out, for example, in the presence of catalytically activated hydrogen, preferably in the presence of Raney-nickel, in an organic solvent such as an alcohol, preferably ethanol, at a temperature in the range of from room temperature to about 100° C. and at a pressure of 1–100 atmospheres. Conveniently, formic acid, sodium cyanoborohydride, sodium borohydride or the borane-dimethylamine complex can be utilized as the reducing agent. The choice of solvent as well as the usual working conditions, for example, temperature, depend primarily on the reducing agent used. When sodium cyanoborohydride is used as the reducing agent, the reductive amination is preferably carried out in methanol at room temperature and at a pH between 6 and 8. When the borane-dimethylamine complex is used as the reducing agent, the reductive amination is preferably carried out in glacial acetic acid at a temperature in the range of from room temperature to the reflux temperature of the mixture. When formic acid is used as the reducing agent, it then preferably also serves as the solvent. The reductive amination in the presence of formic acid is preferably carried out at a temperature in the range of from about 100° C. to about 150° C. The reductive amination in the presence of sodium borohydride is carried out in a suitable organic solvent, for example, an alcohol, preferably at room temperature. Since a re-esterification can occur in the case where a compound of formula II, wherein the group —COZ is an ester group, is reductively aminated in the presence of sodium borohydride, the choice of the solvent in this case depends to a large extent on the starting material of formula II used.

The reaction of a compound of formula IV with an amine of formula V in accordance with process embodiment (b) is carried out according to known methods; expediently in the presence of an excess of the amine of formula V. The reaction is carried out in an inert organic solvent, for example, an aromatic hydrocarbon such as benzene or toluene, a chlorinated hydrocarbon such as methylene chloride, an ether such as diethyl ether, and the like. The reaction is preferably carried out in the presence of an acid-binding agent. Suitable bases for this purpose are, for example, potassium carbonate, sodium carbonate, and the like. The temperature and pressure at which the reaction is carried out are not critical. The reaction is preferably carried out at a temperature in the range of from about 0° C. to about the reflux temperature of the reaction mixture. When a gaseous amine of formula V is used, the reaction is expediently carried out under pressure, for example, at a pressure of 1–100 atmospheres. On the other hand, when a liquid amine is used, the reaction is carried out at normal pressure for reasons of expediency. When the reaction is carried out at normal pressure, it is preferably also carried out under reflux conditions.

The reaction of a compound of formula VI with a compound of formula VII according to process embodiment (c) is carried out according to known methods; expediently in the presence of an excess of the compound of formula VII. The reaction is carried out in an inert organic solvent, for example, dimethylformamide, dimethylsulfoxide, diethyleneglycol dimethyl ether, hexamethylphosphoric acid triamide, and the like. Dimethylformamide is the preferred solvent. The reaction is preferably carried out at a temperature in the range of from about 0° C. to about 100° C., more preferably in the range of from about 40° C. to about 70° C. The reaction is preferably carried out after first converting the compound of formula VI into a corresponding 2-alkali metal derivative. The 2-alkali metal derivatives, of which the 2-sodio derivatives are preferred, are prepared according to methods known using agents which are customarily utilized for this purpose, for example, sodium hydride, sodium ethylate and the like.

The reduction of a compound of formula VIII in accordance with process embodiment (d) can be carried out according to known methods using an electrophilic hydride reducing agent such as diborane, diisobutylaluminum hydride and the like, preferably diborane. The reduction is carried out in an inert organic solvent, preferably diethyl ether or tetrahydrofuran, at a temperature in the range of from about 0° C. to the reflux temperature of the reduction mixture, preferably at the reflux temperature.

The reaction of a benzodiazepine derivative of formula IX with a strong base and a compound of formula VII in accordance with process embodiment (e) is carried out according to known methods in the presence of an inert organic solvent such as dimethylformamide, dimethylsulfoxide, hexamethylphosphoric acid triamide and the like. Dimethylformamide is the preferred solvent. The reaction is carried out in an inert gas atmosphere, preferably under nitrogen, at a temperature in the range of from about −20° C. to about 100° C., preferably in the range of from about 50° C. to about 80° C. Suitable strong bases for this reaction include sodium hydride, potassium tertiary butylate and the like.

The reductive amination of a compound of formula X in accordance with process embodiment (f) is carried out according to known methods by reacting a compound of formula X with an amine of formula V, wherein $R_5$ is hydrogen and $R_6$ is hydrogen, alkyl, cycloalkyl, cycloalkylalkyl, alkoxyalkyl or aralkyl, in the presence of a suitable reducing agent. Thus, the reductive amination can be carried out, for example, in the presence of catalytically activated hydrogen, preferably in the presence of Raney-nickel, in an organic solvent, for example, an alcohol, preferably ethanol, at a temperature in the range of from about room temperature to about 100° C. and at a pressure of 1–100 atmospheres. Conveniently, formic acid, sodium cyanoborohydride, sodium borohydride or the borane-dimethylamine complex can be used as the reducing agent. The choice of the solvent as well as the usual working conditions, for example, temperature, primarily depends on the reducing agent used. The reductive amination in the presence of sodium cyanoborohydride is preferably carried out, for example, in methanol at room temperature and a pH between 6 and 8. The reductive amination in the presence of the borane-dimethylamine complex is preferably carried out, for example, in glacial acetic acid at a temperature in the range of from room temperature to the reflux temperature of the mixture. When formic acid is used as the reducing agent, it also preferably serves as the solvent. When the reductive amination is carried out in the presence of formic acid, the preferred temperature range is from about 100° C. to about 150° C. The reductive amination in the presence of sodium borohydride is preferably carried out in a suitable organic solvent, for example, an alcohol, preferably at room temperature. Since a re-esterification can occur when a starting material of formula X which carries an ester group in the 1-position is reductively aminated in the presence of sodium borohydride, the choice of the alcohol in this case depends on the starting material of formula X used.

The N-substitution of a compound of formula Ia in accordance with process embodiment (g) is carried out according to known methods; for example, by reacting a compound of formula Ia with a suitable alkylating, cycloalkylating, cycloalkylalkylating, hydroxyalkylating, alkoxyalkylating or aralkylating agent in the presence of an acid-binding agent such as sodium carbonate, potassium carbonate, and the like, in an organic solvent, for example, a tertiary alcohol such as tertiary butanol, a hydrocarbon such as benzene or toluene, an ether such as diethyl ether, dioxane or tetrahydrofuran, dimethylformamide, dimethylsulfoxide and the like. However, an excess of an amine of formula Ia can also be used as the acid-binding agent. The reaction is expediently carried out at a temperature in the range of from about 0° C. to about 50° C., preferably at room temperature. Suitable agents for the N-substitution of compounds of formula Ia are compound of the formula

wherein $R_{12}$ is alkyl, cycloalkyl, cycloalkylalkyl, hydroxyalkyl, alkoxyalkyl or aralkyl and X is as previously described.

Compounds of formula Ia can also be converted into corresponding compounds of formula I wherein $R_5$ and $R_6$, independently, are hydrogen, alkyl, cycloalkyl, cycloalkylalkyl or aralkyl, provided that at least one of $R_5$ and $R_6$ is other than hydrogen, by reacting a compound of formula Ia with a corresponding aldehyde or ketone in the presence of either formic acid or catalytically activated hydrogen.

The cleavage of the protecting group in a compound of formula XI in accordance with process embodiment (h) is carried out according to a variety of known methods depending on the nature of the protecting group present. When the protecting group is acyl or carbalkoxy, then the cleavage is carried out under the conditions customarily utilized for acidic hydrolysis or alkaline hydrolysis; for example, in the presence of an ethanolic solution of hydrochloric acid, sodium hydroxide or potassium hydroxide at a temperature in the range of from about 50°C. to the reflux temperature of the reaction mixture. The cleavage of the carbobenzoxy can be carried out, for example, with hydrobromic acid in glacial acetic acid or by catalytic hydrogenation. The benzyl group is preferably cleaved hydrogenolytically.

The reduction of a compound of formula XII in accordance with process embodiment (i) can be carried out in a known manner using an electrophilic hydride reducing agent such as diborane, diisobutylaluminum hydride and the like, preferably diborane. The reduction is carried out in an inert organic solvent, for example, an ether or a hydrocarbon, preferably diethyl ether or tetrahydrofuran, at a temperature in the range of from about 0° C. to the reflux temperature of the reduction mixture, preferably at the reflux temperature.

The compounds of formula I are basic and can be converted into pharmaceutically acceptable acid addition salts. Such salts are, for example, those formed with organic acids such as oxalic acid, citric acid, acetic acid, lactic acid, maleic acid, fumaric acid, ascorbic acid, salicylic acid, tartaric acid or the like, and with inorganic acids such as hydrochloric acid, hydrobromic acid, sulfuric acid, phosphoric acid or the like.

The preparation of compounds of formula II wherein Z is the group -OR, that is, compounds of formula IIa, is illustrated in formula scheme I hereinafter and the preparation of compounds of formula II wherein Z is the group

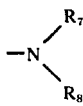

that is, compounds of formula IIb, is illustrated in formula scheme II hereinafter. In these formula schemes, R, $R_1$, $R_2$, $R_3$, $R_4$, $R_7$ and $R_8$ are as previously described and $R'_7$ and $R'_8$, independently, are alkyl, cycloalkyl, cycloalkylalkyl, alkoxyalkyl or aralkyl.

Formula Scheme I

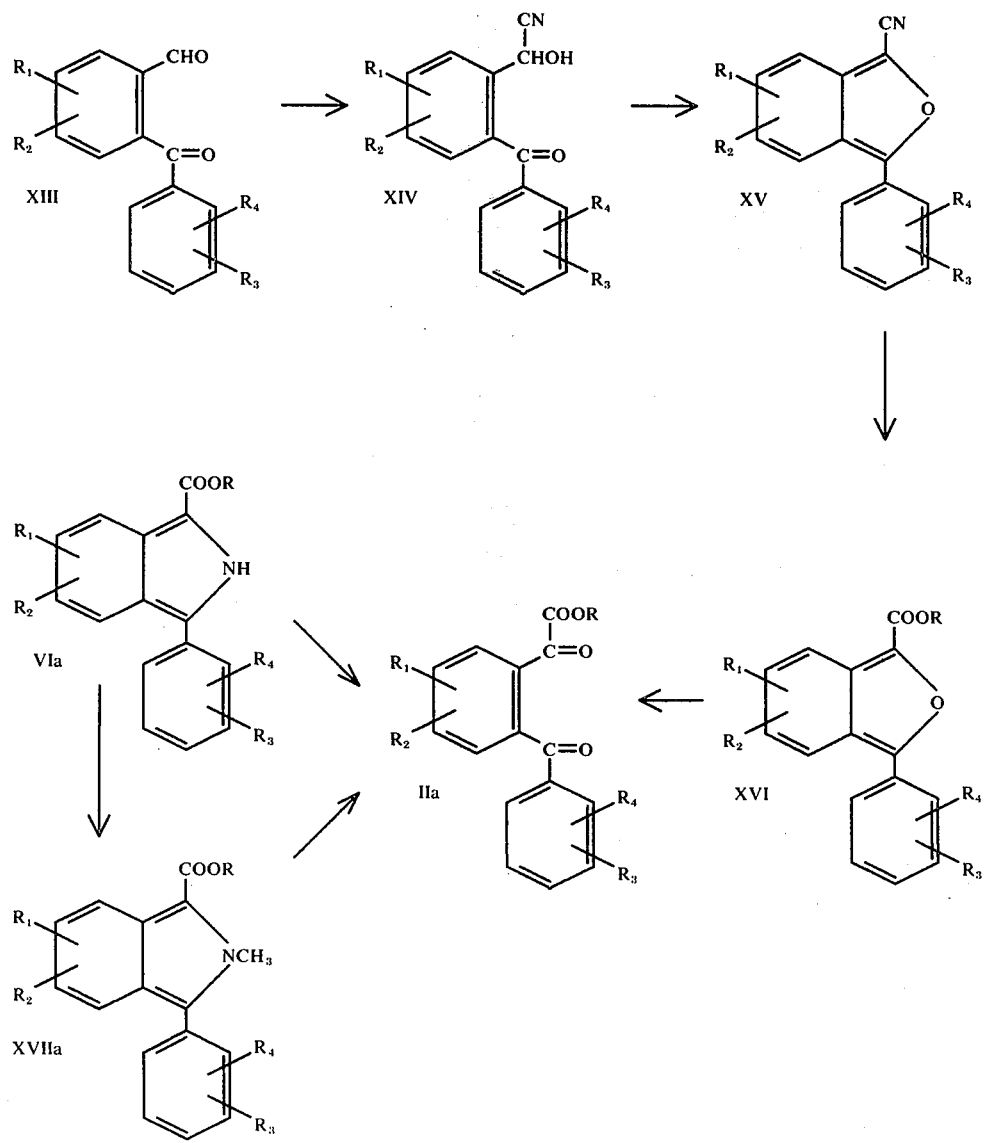

Formula Scheme II

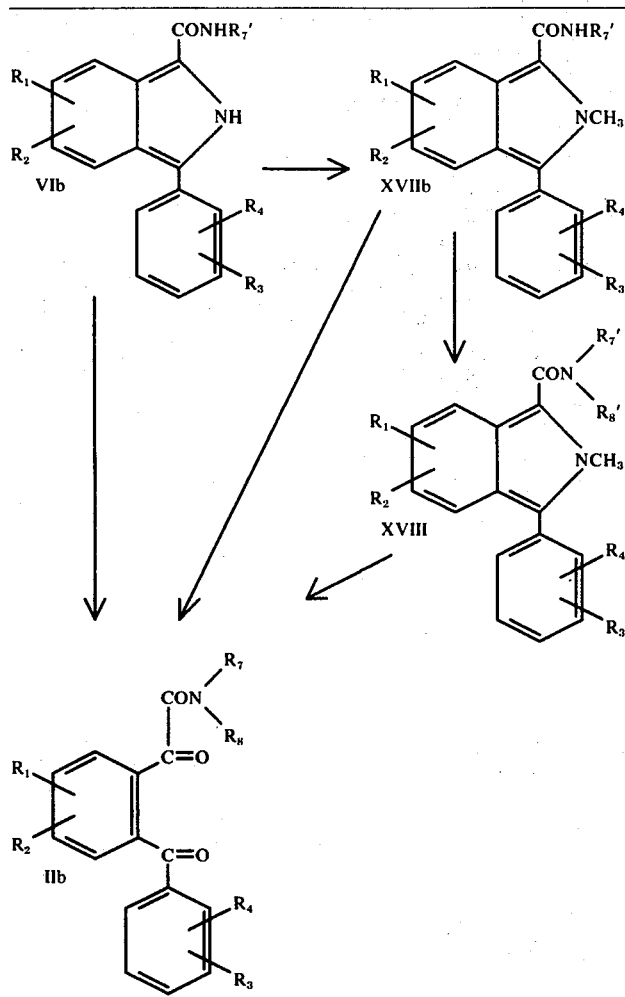

Referring to Formula Scheme I, the o-benzoyl-benzaldehydes of formula XIII are known compounds or can be obtained in an analogous manner to the known compounds.

In the first step of Formula Scheme I, an o-benzoyl-benzaldehyde of formula XIII is reacted in a known manner with hydrocyanic acid or with sodium cyanide or potassium cyanide in the presence of a mineral acid, for example, sulfuric acid, to give a cyanohydrin of formula XIV. Alternatively, an O-benzoylbenzaldehyde of formula XIII is converted into a bisulfite addition compound and this is then treated with an equivalent amount of sodium cyanide to give a cyanohydrin of formula XIV.

In the second step, a cyanohydrin of formula XIV is cyclized to a 1-cyanoisobenzofuran of formula XV according to known methods; for example, by treatment with an inorganic acid such as hydrochloric acid or an organic acid such as glacial acetic acid at a temperature in the range of from about 0° C. to room temperature.

A 1-cyano-isobenzofuran of formula XV can then be converted in a known manner via a corresponding iminoether into an ester of formula XVI. This conversion is carried out, for example, by treating a 1-cyano-isobenzofuran of formula XV with alcoholic hydrochloric acid at room temperature and subsequently hydrolyzing the resulting iminoether to the ester. It will be appreciated that the choice of the alcohol depends on the desired group R in the ester group. If desired, the ester can be prepared by re-esterification of a lower alkyl ester in a known manner.

An ester of formula XVI can then be oxidized to the desired compound of formula IIa in a known manner using a mild oxidizing agent, for example, a ceric salt such as ceric ammonium nitrate, ceric nitrate or ceric sulfate, manganese dioxide or oxygen in a suitable organic solvent such as glacial acetic acid or the like at a temperature in the range of from about 0° C. to the reflux temperature of the reaction mixture, preferably at the reflux temperature. In place of an ester of formula XVI, a corresponding compound of formula VIa or XVIIa can be oxidized to a compound of formula IIa in the manner described earlier. The preparation of compounds of formulas VIa and XVIIa is described hereinafter.

Referring to Formula Scheme II hereinbefore, compounds of formula IIb can be prepared by oxidizing a corresponding compound of formula VIb, XVIIb or XVIII. The oxidation is carried out using the same oxidizing agents and under the same conditions as mentioned earlier in connection with the oxidation of an ester of formula XVI.

Compounds of formula VI wherein Z is the group —OR or —NHR$_7$, R and R$_7$ are as previously described, that is, compounds of formulas VIa and VIb, can be prepared from compounds of the formula

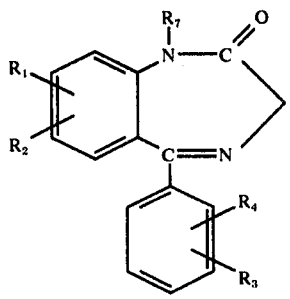 XIX wherein R$_1$, R$_2$, R$_3$, R$_4$ and R$_7$ are as previously described, by reaction in an inert organic solvent such as dimethylformamide, dimethylsulfoxide, hexamethylphosphoric acid triamide or the like, if desired in the presence of a carbonic acid ester of the formula

CO(OR)$_2$ wherein R is as previously described, with a strong base such as sodium hydride, potassium tertiary butylate or the like. The reaction is preferably carried out under an atmosphere of nitrogen at a temperature in the range of from about −20° C. to about 100° C., preferably in the range of from about 50° to about 80° C. When the reaction is carried out in the presence of a carbonic acid ester, there is obtained a compound of formula VI, wherein Z is the group —OR. On the other hand, when the reaction is carried out in the absence of a carbonic acid ester, there is obtained a corresponding amide, that is, a compound of formula VI, wherein Z is the group —NHR$_7$. A compound of formula VI need not be isolated before being reacted further, for example, with a compound of formula VII. Conveniently, the further reaction, e.g. with a compound of formula VII, can be carried out in the reaction medium wherein the compound of formula VI is prepared.

Compounds of formula VI wherein Z is the group

wherein R$_7$ and R$_8$ are other than hydrogen can be prepared in a known manner by reductively aminating a corresponding N,N-disubstituted compound of formula IIb with ammonia. Conveniently, the compound of formula IIb is reductively aminated with ammonium formate in formic acid at the reflux temperature of the mixture.

Compounds of formula XVIIa and XVIIb can be prepared in a known manner by reacting compounds of formulas VIa and VIb with, for example, methyl tosylate or dimethylsulfate. This reaction is expediently carried out in the presence of an inert organic solvent, for example, dimethylformamide, dimethylsulfoxide, hexamethylphosphoric acid triamide or the like, at normal pressure and room temperature. The compound of formula VIa or VIb is previously converted into a corresponding 2-alkali metal derivative. The 2-alkali metal derivatives, of which the 2-sodio derivatives are preferred, are prepared according to known methods using agents which are customarily utilized for this purpose, for example, sodium hydride, sodium ethylate and the like.

Compounds of formula XVIII can be prepared according to known methods by reacting compounds of formulas XVIIa and XVIIb with a suitable alkylating agent such as an alkyl iodide, dialkylsulfate or the like. The reaction is expediently carried out in the presence of an inert organic solvent such as dimethylformamide, dimethylsulfoxide, hexamethylphosphoric acid triamide or the like, at normal pressure and at a temperature in the range of from about room temperature to about 80° C. The compounds of formulas XVIIa and XVIIb are previously converted into the corresponding N-alkali metal derivatives using agents which are customarily utilized for this purpose such as potassium tertiary butylate, sodium hydride and the like.

The compounds of formula IV can be prepared by reacting a compound of formula VI with a compound of the formula

X—A—X wherein A is as previously described and each X is a leaving atom or group. The reaction is conveniently carried out in the presence of an inert organic solvent, for example, dimethylformamide, dimethylsulfoxide, hexamethylphosphoric acid triamide, nitromethane, N-methylpyrrolidone or the like, at normal pressure and at room temperature. A compound of formula VI is previously converted into a corresponding 2-alkali metal derivative. The 2-alkali metal derivatives, of which the 2-sodio derivatives are preferred, are prepared according to known methods using agents which are customarily utilized for this purpose such as sodium hydride, sodium ethylate and the like.

The compounds of formula VIII can also be prepared from compounds of formula VI; for example, by reacting a compound of formula VI wherein Z is the group —OR, wherein R is as previously described, in a known manner with an ω-haloalkanecarboxylic acid amide of the formula

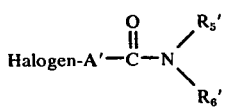

wherein A', R'$_5$ and R'$_6$ are as previously described. The reaction is carried out in an inert organic solvent, for example, dimethylformamide, dimethylsulfoxide, diethyleneglycol dimethyl ether, hexamethylphosphoric acid triamide or the like, at a temperature in the range of from about 0° C. to 100° C., preferably in the range of from about 50° C. to about 80° C. The reaction is carried out after the prior conversion of a compound of formula VI into a corresponding 2-alkali metal derivative which is prepared according to known methods using agents customarily utilized for this purpose, for example, sodium hydride or sodium ethylate. The preferred 2-alkali metal derivative in the 2-sodio derivative.

The compounds of formula X can be prepared, for example, by reacting a compound of formula VI wherein Z is the group -OR in a known manner with a compound of the formula

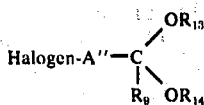

wherein A″ and $R_9$ are as previously described and $R_{13}$ and $R_{14}$, independently, are alkyl, or taken together, are $-CH_2-CH_2-$ or $-CH_2-CH_2-CH_2-$, to produce a compound of the formula

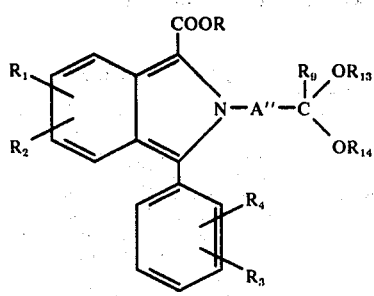

XX wherein A″, $R_1$, $R_2$, $R_3$, $R_4$, $R_9$, $R_{13}$, $R_{14}$ and R are as previously described, which is then hydrolyzed in a known manner to give a compound of formula X. The first step, that is, the reaction is carried out in an inert organic solvent, for example, dimethylformamide, dimethylsulfoxide, hexamethylphosphoric acid triamide or the like, at a temperature in the range of from about 0° C. to about 100° C., preferably in the range of from about 50° C. to about 80° C., the compound of formula VI having been previously converted into a corresponding 2-alkali metal derivative, preferably the 2-sodio derivative, using an agent customarily utilized for this purpose, for example, sodium hydride or sodium ethylate. The second step, that is, the hydrolysis of the compound of formula XX, is carried out according to known methods; for example, by treatment with ethanolic hydrochloric acid, ethanolic p-toluenesulfonic acid or the like at a temperature in the range of from about 0° C. to about 100° C., expediently at about room temperature.

The compounds of formula XI can be prepared, for example, by reacting a compound of formula VI with a compound of the formula

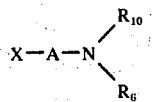

wherein A, X, $R_6$ and $R_{10}$ are as previously described. The reaction can be carried out under the conditions described earlier for the reaction of a compound of formula VI with a compound of formula VII.

The compound of formula XII can be prepared by acylating a corresponding compound of formula I wherein $R_5$ is hydrogen, alkyl, cycloalkyl, cycloalkylalkyl, alkoxyalkyl, aryl or aralkyl, and $R_6$ is hydrogen at the nitrogen atom in a known manner using a suitable acylating agent, for example, an acid chloride or acid anhydride.

The compounds of formulas III, V, VII and X are known or can be prepared in an analogous manner to the known compounds.

The novel starting materials also form part of the present invention.

The isoindole derivatives provided by this invention, that is, the compounds of formula I and their pharmaceutically acceptable acid addition salts, can be used as medicaments. More particularly, they possess, for example, a pronounced anorectic activity and are therefore useful as appetite-suppressants. Significantly also, in contrast to other known appetite-suppressants, the compounds of formula I have practically no central-stimulating activity. The anorectic activity of the compounds of formula I is demonstrated by administering a compound of formula I to be tested in four doses of 300 μ mol/kg. or less in 5% gum arabic orally to groups each comprising 6 male rats which are given food ad libitum in the test for 48 hours. Then, 24 and 48 hours after the first administration, the food consumption is determined by weighing the food vessels and making a comparison with the food consumption of untreated control animals (100%). The $ED_{65}$ denotes the dose in mg/kg. of the compound of formula I which reduces the food consumption to 65% of that of the controls. Thus, for example, 5-chloro-2-[2-diethylamino)ethyl]-3-phenylisoindole-1-carboxylic acid ethyl ester (Compound A) has an $ED_{65}$ of 42 mg/kg., 5-chloro-2-[3-(diethylamino)-propyl]-3-phenylisoindole-1-carboxylic acid ethyl ester (Compound B) has an $ED_{65}$ of 35 mg/kg. and 5-chloro-3-(p-chlorophenyl)-2-[2-diethylamino)ethyl]-isoindole-1-carboxylic acid ethyl ester (Compound C) has an $ED_{65}$ of 27 mg/kg. The toxicity values ($LD_{50}$) were determined according to standard methods in mice and exemplary of the results are: 1250 mg/kg. for Compounds A and B and 2500 mg/kg for Compound C.

The isoindole derivatives of formula I provided by the invention can be used as medicaments, for example, in the form of pharmaceutical preparations which contain them in association with compatible pharmaceutical carrier materials. Such carrier materials can comprise an organic or inorganic, inert carrier material suitable for enteral or parenteral administration such as, for example, water, gelatine, gum arabic, lactose, starch, magnesium stearate, talc, vegetable oils, polyalkyleneglycols, petroleum jelly or the like. The pharmaceutical preparations can be made up in a solid form, for example, as tablets, dragees, suppositories or capsules, or in a liquid form, as solutions, suspensions or emulsions. The pharmaceutical preparations may be sterilized and/or may contain adjuvants such as preservatives, stabilizers, wetting agents, emulsifiers, salts for varying the osmotic pressure or buffers. The pharmaceutical preparations can also contain other therapeutically valuable substances.

Conveniently, pharmaceutical dosage forms contain about 1 to 30 mg. of a compound of formula I. Conveniently, oral dosage ranges comprise from about 0.1 mg/kg. per day to about 0.5 mg/kg. per day. The aforementioned range can, however, be increased or decreased depending on individual requirements of the patient.

The Examples which follow further illustrate the invention. All temperatures are in degrees Centigrade, unless otherwise stated.

EXAMPLE 1

Preparation of
5-chloro-2-[2-(diethylamino)ethyl]-3-phenylisoindole-1-carboxylic acid ethyl ester hydrochloride A solution of 30.0 g. of 5-chloro-3-phenylisoindole-1-carboxylic acid ethyl ester in 500 ml. of dimethylformamide is treated under nitrogen at -10° C. with 0.11 mol. of sodium hydride (5.0 g. of a 55% dispersion in mineral oil) and then stirred in an ice-bath for 30–40 minutes.

Meanwhile, in a second flask, 4.6 g. of sodium are dissolved in 100 ml. of ethanol and treated at 0° C. with 34.5 g. of 2-diethylaminoethyl chloride hydrochloride. After dilution with 50 ml. of dimethylformamide and stirring for 30–40 minutes in an ice-bath, the obtained fine suspension is added dropwise at 0°–2° C. over a period of 15–20 minutes to the sodium derivative of 5-chloro-3-phenylisoindole-1-carboxylic acid ethyl ester prepared as in the foregoing paragraph. The mixture is subsequently stirred for 30 minutes at room temperature and then heated at 60° C. for 3 hours. After cooling, the mixture is poured into 4 liters of ice-water, 200 g. of sodium chloride are added and the separated oily product is immediately extracted with methylene chloride. The organic phase, shielded from daylight, is washed with a saturated aqueous solution of sodium chloride, dried over sodium sulfate and concentrated to dryness. The resulting oil is then taken up in 200 ml. of ether, treated with 280 ml. of 0.5-N hydrochloric acid and thoroughly shaken. After cooling in an ice-bath, the crystallized hydrochloride is removed by filtration under suction, washed with water and ether and then dissolved in 700 ml. of methylene chloride. The aqueous layer is separated; the organic phase is dried over sodium sulfate, filtered and treated portionwise with 450 ml. of ether, whereby there is obtained 5-chloro-2-[2-(diethylamino)ethyl]-3-phenylisoindole-1-carboxylic acid ethyl ester hydrochloride in the form of colorless crystals having a melting point of 248°–250° C. (decomposition). Crystallization from methylene chloride/ether does not increase the melting point.

In order to obtain the free base, the previously obtained hydrochloride is treated with 2-N sodium carbonate in the presence of ether. The ethereal extract, shielded from light, is washed with water, dried over sodium sulfate and evaporated. The residue crystallizes on trituration with ether. Recrystallization from n-hexane yields colorless crystals of 5-chloro-2-[2-(diethylamino)ethyl]-3-phenylisoindole-1-carboxylic acid ethyl ester having a melting point of 75°–77° C.

The starting material can be prepared as follows:
A solution of 28.5 g. of 7-chloro-1,3-dihydro-1-methyl-5-phenyl-2H-1,4-benzodiazepin-2-one in 400 ml. of dimethylformamide is treated under nitrogen at −10° C. with 0.25 mol. of sodium hydride (11.0 g. of a 55% dispersion in mineral oil) and stirred at the same temperature for 15 minutes. The suspension is then treated at −10° C. to −5° C. with a solution of 35.5 g. of diethylcarbonate in 50 ml. of dimethylformamide. The mixture is stirred firstly for 1 hour at 20° C., then for an additional 4 hours at 60° C. and finally poured onto a mixture of 100 g. of sodium chloride and 2.5 kg. of ice. The precipitate is removed by filtration, washed with water and dissolved in methylene chloride. The organic solution, shielded from daylight, is washed with a saturated aqueous solution of sodium chloride, dried over sodium sulfate and concentrated to dryness. The crystalline residue is heated to reflux with 500 ml. of ethanol for 10 minutes and then cooled in an ice-bath. After filtering and washing with ethanol and ether, there is obtained 5-chloro-3-phenylisoindole-1-carboxylic acid ethyl ester in the form of greenish crystals; melting point 208°–210° C. (decomposition). Crystallization from acetonitrile does not increase the melting point.

In a manner analogous to that described above, the following isoindole derivatives can be prepared:

| Alkylating agent | Isoindole derivative |
| --- | --- |
| 2-dibutylaminoethyl chloride | 5-chloro-2-[2-(dibutylamino)ethyl]-3-phenylisoindole-1-carboxylic acid ethyl ester hydrochloride; melting point 232°–234° C (decomposition) |
| 1-chloro-2-dimethylamino-2-methylpropane | 5-chloro-2-[2-(dimethylamino)-2-methylpropyl]-3-phenylisoindole-1-carboxylic acid ethyl ester hydrochloride; melting point 218°–220° C. (decomposition) |
| 4-(2-chloroethyl)morpholine | 5-chloro-2-(2-morpholino-ethyl)-3-phenylisoindole-1-carboxylic acid ethyl ester hydrochloride; melting point 226°–228° C. (decomposition) |

EXAMPLE 2

Preparation of
2-[2-(diethylamino)ethyl]-3-phenylisoindole-1-carboxylic acid ethyl ester hydrochloride A solution of 26.5 g. of 3-phenylisoindole-1-carboxylic acid ethyl ester in 600 ml. of dimethylformamide is treated under nitrogen at −10° C. with 0.40 mol. of sodium hydride (17.5 g. of a 55% dispersion in mineral oil) and stirred at the same temperature for 15 minutes. Then, at −10° C. to −5° C. there are added 34.5 g. of 2-diethylaminoethyl chloride hydrochloride. The mixture is stirred for 1 hour at room temperature and subsequently heated for 3 hours at 60° C. The mixture is cooled and poured into 8 liters of ice-water. After the addition of 300 g. of sodium chloride, the oily precipitate is separated by decantation and immediately dissolved in methylene chloride. The solution, shielded from daylight, is washed with a saturated aqueous solution of sodium chloride, dried over sodium sulfate and concentrated to dryness. The resulting oil is dissolved in 200 ml. of ether, treated with 280 ml. of 0.5-N hydrochloric acid and thoroughly shaken. After cooling in an ice-bath, the separated hydrochloride is removed by filtration under suction, washed with water and ether and then dissolved in methylene chloride. The aqueous layer is separated and the methylene chloride solution is dried over sodium sulfate and filtered. After the addition of ether, there is obtained 2-[2-(diethylamino)ethyl]-3-phenylisoindole-1-carboxylic acid ethyl ester hydrochloride; melting point 230°–232° C. (decomposition).

The starting material can be prepared from 1,3-dihydro-1-methyl-5-phenyl-2H-1,4-benzodiazepin-2-one and diethylcarbonate in a manner analogous to that described in Example 1. After recrystallization from ethanol, there is obtained 3-phenylisoindole-1-carboxylic acid ethyl ester; m.p. 144°–147° C (decomposition).

EXAMPLE 3

Preparation of
5-chloro-2-[2-(diethylamino)ethyl]-3-phenylisoindole-1-carboxylic acid methyl ester hydrochloride In a manner analogous to that described in Example 2, from 28.5 g. of 5-chloro-3-phenylisoindole-1-carboxylic acid methyl ester and 34.5 g. of 2-diethylaminoethyl chloride hydrochloride, there is obtained a solid crude product which, after recrystallization from chloroform/ether, yields 5-chloro-2-[2-(diethylamino)ethyl]-3-phenylisoindole-1-carboxylic acid methyl ester hydrochloride having a melting point of 247°–250° C. (decomposition).

The starting material can be prepared from 7-chloro-1,3-dihydro-1-methyl-5-phenyl-2H-1,4-benzodiazepin-2-one and dimethylcarbonate in a manner analogous to that described in Example 1. After recrystallization from acetone, there is obtained 5-chloro-3-phenylisoindole-1-carboxylic acid methyl ester; melting point 208°–210° C. (decomposition).

EXAMPLE 4

Preparation of
5-chloro-2-[2-(diethylamino)ethyl]-3-phenylisoindole-1-carboxylic acid ethyl ester hydrochloride A solution of 28.5 g. of 7-chloro-1,3-dihydro-1-methyl-5-phenyl-2H-1,4-benzodiazepin-2-one in 400 ml. of dimethylformamide is treated under nitrogen at −10° C. with 0.25 mol. of sodium hydride (11.0 g. of a 55% dispersion in mineral oil) and stirred at the same temperature for 15 minutes. The suspension is then treated at a temperature between −10° C. and −5° C. with a solution of 35.5 g. of diethylcarbonate in 50 ml. of dimethylformamide. The mixture is stirred firstly for 1 hour at 20° C. and then for 4 hours at 60° C. Thereafter, the mixture is allowed to stand overnight at room temperature under an atmosphere of nitrogen.

In a second flask, 2.3 g. of sodium are dissolved in 80 ml. of ethanol and treated at 0° C. with 34.5 g. of 2-diethylaminoethyl chloride hydrochloride; after dilution with 50 ml. of dimethylformamide and stirring for 30 minutes in an ice-bath, the obtained fine suspension is added dropwise at 0°–2° C. over a period of 15–20 minutes to the mixture prepared according to the previous paragraph. The mixture is subsequently stirred for 30 minutes at 20° C., heated for 3 hours at 60° C. and poured into 4 liters of ice-water. After the addition of 200 g. of sodium chloride, the separated oily product is immediately extracted with methylene chloride. The orgainc phase, shielded from daylight, is washed with a saturated aqueous solution of sodium chloride, dried over sodium sulfate and concentrated to dryness under reduced pressure. The resulting oil is then dissolved in 200 ml. of ether, treated with 280 ml. of 0.5-N hydrochloric acid and thoroughly shaken. After cooling in an ice-bath, the crystallized hydrochloride is removed by filtration under suction, washed with water and ether and then dissolved in 500 ml. of methylene chloride. The aqueous layer is separated, the organic phase is dried over sodium sulfate, filtered and treated portionwise with 350 ml. of ether, whereby there is obtained 5-chloro-2-[2-(diethylamino)ethyl]-3-phenylisoindole-1-carboxylic acid ethyl ester hydrochloride; melting point 248°–250° C. (decomposition).

In a manner analogous to that described above, the following isoindole derivatives can be prepared:

| Carbonic acid ester | Isoindole derivative |
| --- | --- |
| dibenzyl carbonate | 5-chloro-2-[2-(diethylamino)ethyl]-3-phenylisoindole-1-carboxylic acid benzyl ester hydrochloride; melting point 236° C. (decomposition) |
| diisobutyl carbonate | 5-chloro-2-[2-(diethylamino)ethyl]-3-phenylisoindole-1-carboxylic acid isobutyl ester hydrochloride; melting point 253° C. (decomposition) |
| diallyl carbonate | 5-chloro-2-[2-(diethylamino)ethyl]-3-phenylisoindole-1-carboxylic acid allyl ester hydrochloride; melting point 252° C. (decomposition) |
| dihexyl carbonate | 5-chloro-2-[2-diethylamino)ethyl]-3-phenylisoindole-1-carboxylic acid hexyl ester hydrochloride; melting point 192° C. (decomposition) |
| dicyclohexyl carbonate | 5-chloro-2-[2-(diethylamino)ethyl]-3-phenylisoindole-1-carboxylic acid cyclohexyl ester hydrochloride; melting point 276° C. (decomposition) |
| bis(2-methoxyethyl)carbonate | 5-chloro-2-[2-diethylamino)ethyl]-3-phenylisoindole-1-carboxylic acid 2-methoxyethyl ester hydrochloride; melting point 227° C (decomposition) |

EXAMPLE 5

Preparation of
5-chloro-2-[2-(diethylamino)ethyl]-3-phenylisoindole-1-carboxylic acid ethyl ester hydrochloride A solution of 27.2 g. of 7-chloro-2,3-dihydro-2-oxo-5-phenyl-1H-1,4-benzodiazepine-3-carboxylic acid ethyl ester in 480 ml. of dimethylformamide is treated under nitrogen at −10° C. with 0.33 mol. of sodium hydride (14.4 g. of a 55% dispersion in mineral oil) and stirred at the same temperature for 15 minutes. To this mixture, there are added at −10° C. to −5° C. 27.2 g. of 2-diethylaminoethyl chloride hydrochloride; the mixture is then stirred at room temperature for 1 hour and subsequently heated for 3 hours at 60° C. After cooling, the mixture is poured into 4 liters of ice-water with stirring; 200 g. of sodium chloride are added and the oily precipitate is separated be decantation. The latter is immediately dissolved in methylene chloride and the organic solution, shielded from daylight, is washed with a saturated aqueous solution of sodium chloride, dried over sodium sulfate and concentrated to dryness. The resulting oil is dissolved in 100 ml. of ether and filtered; the filtrate is treated with 180 ml. of 0.5-N hydrochloric acid and throughly shaken. After cooling in an icebath, the crystallized hydrochloride is removed by filtration, washed with water and ether and then dissolved in 200 ml. of methylene chloride. After separation of the aqueous layer, the methylene chloride solution is dried over sodium sulfate, filtered and treated portionwise with 150 ml. of ether, whereby there is obtained 5-chloro-2-[2-(diethylamino)ethyl]-3-phenylisoindole-1-carboxylic acid ethyl ester hydrochloride; melting point 248°–250° C. (decomposition).

In a manner analogous to that described above, the following isoindole derivatives can be prepared:

| Alkylating agent | Isoindole derivative |
|---|---|
| 3-diethylamino-1-propyl-chloride | 5-chloro-2-[3-(diethylamino)propyl]-3-phenylisoindole-1-carboxylic acid ethyl ester hydrochloride; melting point 203°–206° C. (decomposition) |
| 2-disiopropylamino-ethyl-chloride | 5-chloro-3-[2-(diisopropylamino)-ethyl]-3-phenylisoindole-1-carboxylic acid ethyl ester hydrochloride; melting point 237°–239° C. (decomposition) |
| ethylbenzylaminoethyl-chloride | 2-[2-(ethylbenzylamino)-ethyl]-5-chloro-3-phenylisoindole-1-carboxylic acid ethyl ester hydrochloride; melting point 210°–213° C. (decomposition) |

EXAMPLE 6

Preparation of 5-chloro-3-phenyl-2-[2-(1-pyrrolidinyl)ethyl]-isoindole-1-carboxylic acid ethyl ester hydrochloride According to the procedure described in Example 5, 27.2 g. of 7-chloro-2,3-dihydro-2-oxo-5-phenyl-1H-1,4-benzodiazepine-3-carboxylic acid ethyl ester are reacted with 27.2 g. of N-(2-chloroethyl)-pyrrolidine hydrochloride. After cooling, the mixture is poured into 4 liters of ice-water; 200 g. of sodium chloride are added thereto and the separated product is immediately extracted with chloroform. The organic phase, shielded from daylight, is washed with a saturated aqueous solution of sodium chloride, dried over sodium sulfate and concentrated to dryness. The resulting oil is taken up in ether and the filtered solution shaken with an excess of 0.5-N hydrochloric acid. The clear aqueous phase is made alkaline with 2-N ammonium hydroxide; the liberated base is extracted with chloroform and the extract dried over sodium sulfate and then evaporated to dryness. The resulting oil is chromatographed on 700 g. of silica gel with ethyl acetate as the eluant. The homogeneous fractions are combined, concentrated, takne up in ether and treated with ethereal hydrochloric acid in excess. The hydrochloride is removed by filtration and washed with ether. After recrystallization from methylene chloride/ether, there is obtained 5-chloro-3-phenyl-2-[2-(1-pyrrolidinyl)ethyl]-isoindole-1-carboxylic acid ethyl ester hydrochloride; melting point 187°–190° C. (decomposition).

In a manner analogous to that described above, the following isoindole derivatives can be prepared:

| Alkylating agent | Isoindole derivative |
|---|---|
| dimethylaminoethyl chloride | 5-chloro-2-[2-(dimethylamino)ethyl]-3-phenylisoindole-1-carboxylic acid ethyl ester hydrochloride; melting point 192°–194° C. (decomposition) |
| 2-chloro-1-dimethylamino-propane | 5-chloro-2-[2-(dimethylamino)propyl]-3-phenylisoindole-1-carboxylic acid ethyl ester hydrochloride; melting point 251°–253° C. (decomposition) |

EXAMPLE 7

Preparation of 5-chloro-2-[2-(diethylamino)ethyl]-3-phenylisoindole-1-carboxylic acid isopropyl ester hydrochloride In a manner analogous to that described in Example 5, from 14.3 g. of 7-chloro-2,3-dihydro-2-oxo-5-phenyl-1H-1,4-benzodiazepine-3-carboxylic acid isopropyl ester and 13.6 g. of 2-diethylaminoethyl chloride hydrochloride, there is obtained a solid crude product which, after recrystallization from methylene chloride/ether, yields 5-chloro-2-[2-(diethylamino)ethyl]-3-phenylisoindole-1-carboxylic acid isopropyl ester hydrochloride having a melting point of 256°–260° C. (decomposition).

The starting material can be prepared as follows:

500 Ml. of propanol-(2) are treated with 14 g. of sodium methylate; the methanol formed is removed by concentration in vacuo to half the volume and the suspension obtained is diluted with 250 ml. of methylene chloride. Then, 34.2 g. of 7-chloro-2,3-dihydro-2-oxo-5-phenyl-1H-1,4-benzodiazepine-3-carboxylic acid ethyl ester are added and the mixture is subsequently stirred at 25° C. for 40 minutes. The orange solution is make acidic with glacial acetic acid and evaporated to dryness under reduced pressure. The residue is partitioned between water and chloroform; the organic phase is washed with a saturated aqueous solution of sodium chloride, dried over sodium sulfate and concentrated to dryness. The solid crude product is triturated with ether, removed by filtration, washed with ether and recrystallized from methylene chloride/ether, whereby there is obtained 7-chloro-2,3-dihydro-2-oxo-5-phenyl-1H-1,4-benzodiazepine-3-carboxylic acid isopropyl ester having a melting point of 234°–238° C. (decomposition).

EXAMPLE 8

Preparation of
6-chloro-2-[2-(diethylamino)ethyl]-3-phenylisoindole-1-carboxylic acid ethyl ester hydrochloride In a manner analogous to that described in Example 5, by reaction of 27.2 g. of 8-chloro-2,3-dihydro-2-oxo-5-phenyl-1H-1,4-benzodiazepine-3-carboxylic acid ethyl ester with 27.2 g. of 2-diethylaminoethyl chloride hydrochloride there is obtained 6-chloro-2-[2-(diethylamino)ethyl]-3-phenylisoindole-1-carboxylic acid ethyl ester hydrochloride which, after recrystallization from methylene chloride/ether, has a melting point of 231°–234° C. (decomposition).

The starting material can be prepared as follows:

A suspension of 45.0 g. of 2-carbethoxy-N-(benzyloxycarbonyl)glycine in 120 ml. of dry methylene chloride, cooled to −20° C., is treated portionwise with 30 g. of phosphorus pentachloride and stirred for 30 minutes at −20° C. to −10° C. To the now clear solution, there is added at the same temperature a solution of 27.7 g. of 2-amino-4-chlorobenzophenone and 1 ml. of dimethylformamide in 120 ml. of dry methylene chloride. The mixture is concentrated under reduced pressure at 40°–45° C. The residue is partitioned between methylene chloride and 10% aqueous soda solution and the methylene chloride phase is dried over sodium sulfate and evaporated to dryness. There is obtained a reddish-colored resin of crude 2'-benzoyl-2-[(benzyloxycarbonyl)amino]-2-carbethoxy-5'-chloroacetanilide, which is then immediately reacted with 130 ml. of a 33% solution of hydrobromic acid in glacial acetic acid. After stirring at room temperature for 90 minutes, the obtained solution is concentrated at 45° C. and the oily residue partitioned between water and ether. The aqueous solution is made weakly alkaline with solid bicarbonate while cooling with ice. The separated base is extracted with methylene chloride and the extracts are dried over sodium sulfate and evaporated to dryness. The resulting oil is dissolved in a mixture of 180 ml. of toluene and 180 ml. of glacial acetic acid and heated at 80° C. for 90 minutes. The solution is concentrated to an oil and is crystallized from ether so that there is obtained 8-chloro-2,3-dihydro-2-oxo-5-phenyl-1H-1,4-benzodiazepine-3-carboxylic acid ethyl ester, having a melting point of 214°–217° C. (decomposition). Recrystallization from acetonitrile does not increase the melting point.

In a manner analogous to that described above, the following isoindole derivatives can be prepared:

| Benzodiazepine derivative | Isoindole derivative |
|---|---|
| 7-chloro-5-(p-chlorophenyl)-2,3-dihydro-2-oxo-1H-1,4-benzodiazepine-3-carboxylic acid ethyl ester; melting point 189°–192° C. (decomposition) | 5-chloro-3-(p-chlorophenyl)-2-[2-(diethylamino)ethyl]-isoindole-1-carboxylic acid ethyl hydrochloride; melting point 225°–228°C. (decomposition) |
| 7,9-dichloro-2,3-dihydro-2-oxo-5-phenyl-1H-1,4-benzodiazepine-3-carboxylic acid ethyl ester; melting point 182°–184° C. (decomposition) | 5,7-dichloro-2-[2-(diethylamino)-ethyl]-3-phenylisoindole-1-carboxylic acid ethyl ester hydrochloride; melting point 197°–199° C. (decomposition) |
| 7-chloro-5-(o-fluorophenyl)-2,3-dihydro-2-oxo-1H-1,4-benzodiazepine-3-carboxylic acid ethyl ester; melting point 192°–194° C. (decomposition) | 5-chloro-2-[2-(diethylamino)ethyl]-3-(o-fluorophenyl)-isoindole-1-carboxylic acid ethyl ester hydrochloride; melting point 228°–230° C. (decomposition) |
| 7-fluoro-2,3-dihydro-2-oxo-5-phenyl-1H-1,4-benzodiazepine-3-carboxylic acid ethyl ester; melting point 226°–230° C. (decomposition) | 2-[2-(diethylamino)-ethyl]-5-fluoro-3-phenylisoindole-1-carboxylic acid ethyl ester hydrochloride; melting point 238°–240° C. (decomposition) |

| Benzodiazepine derivative | Isoindole derivative |
|---|---|
| 5-(p-chlorophenyl)-2,3-dihydro-2-oxo-1H-1,4-benzodiazepine-3-carboxylic acid ethyl ester; melting point 223°–227° C. (decomposition) | 3-(p-chlorophenyl)-2-[2-(diethylamino)ethyl]-isoindole-1-carboxylic acid ethyl ester hydrochloride; melting point 202°–204° C. (decomposition) |
| 2,3-dihydro-7-methyl-2-oxo-5-phenyl-1H-1,4-benzodiazepine-3-carboxylic acid ethyl ester; melting point 229°–231° C. (decomposition) | 2-[2-(diethylamino)-ethyl]-5-methyl-3-phenylisoindole-1-carboxylic acid ethyl ester hydrochloride; melting point 242°–244° C. (decomposition) |
| 2,3-dihydro-2-oxo-5-p-tolyl-1H-1,4-benzodiazepine-3-carboxylic acid ethyl ester; melting point 189°–191° C. (decomposition) | 2-[2-(diethylamino)-ethyl]-3-p-tolyl-isoindole-1-carboxylic acid ethyl ester hydrochloride; melting point 200°–202° C. (decomposition) |
| 2,3-dihydro-7-methyl-2-oxo-5-p-tolyl-1H-1,4-benzodiazepine-3-carboxylic acid ethyl ester; melting point 216°–220° C. (decomposition) | 2-[(diethylamino)ethyl]-5-methyl-3-p-tolylisoindole-1-carboxylic acid ethyl ester hydrochloride; melting point 235°–238° C. (decomposition) |
| 2,3-dihydro-5-(p-methoxyphenyl)-2-oxo-1H-1,4-benzodiazepine-3-carboxylic acid ethyl ester; melting point 187°–192° C. (decomposition) | 2-[2-diethylamino)ethyl]-3-(p-methoxyphenyl)-isoindole-1-carboxylic acid ethyl ester hydrochloride; melting point 188°–191° C. (decomposition) |

EXAMPLE 9

Preparation of 5-chloro-2-[4-(diethylamino)butyl]-3-phenylisoindole-1-carboxylic acid ethyl ester hydrochloride A solution of 8.7 g. of 2-(4-bromobutyl)-5-chloro-3phenylisoindole-1-carboxylic acid ethyl ester in 40 ml. of acetone is treated with 3.0 g. of sodium iodide and 1.6 g. of diethylamine and stirred in the dark at room temperature for 20 hours. After concentration under reduced pressure, the residue is treated at 0°–2° C. with 40 ml. of 1-N sodium hydroxide solution and then extracted with ether. The ethereal extract is immediately shaken with 40 ml. of 0.5-N hydrochloric acid and the acidic aqueous phase is made alkaline at 0°–2° C. with 1-N sodium hydroxide solution. The mixture is immediately extracted with methylene chloride and the organic phase, shielded from daylight, is dried over sodium sulfate. After concentration, the resulting oil is dissolved in ether and treated with ethereal hydrochloric acid. The crystallized hydrochloride is removed by filtration and washed with ether, and there is obtained 5-chloro-2-[4-(diethylamino)butyl]-3-phenylisoindole-1-carboxylic acid ethyl ester hydrochloride; melting point 137°–140° C. Recrystallization from methylene chloride/ether does not increase the melting point.

The starting material can be prepared as follows:

A solution of 12.0 g. of 5-chloro-3-phenylisoindole-1-carboxylic acid ethyl ester in 240 ml. of dimethylformamide is treated under nitrogen at −10° C. with 0.08 mol. of sodium hydride (3.5 g. of a 55% dispersion in mineral oil) and stirred in an ice-bath for 30 minutes. Then, there are added thereto at −10° C. 26.0 g. of 1,4-dibromobutane in one batch; the mixture is thereafter stirred at room temperature for 1 hour and subsequently heated at 60° C. for 18 hours. After cooling, the mixture is poured into 2 liters of ice-water, 100 g. of sodium chloride are added and the separated oily product is immediately extracted with methylene chloride. The organic phase, shielded from daylight, is washed with a solution of sodium chloride, dried over sodium sulfate and evaporated to dryness under reduced pressure. The resulting oil is taken up in chloroform and chromatographed on 500 g. of silica gel with chloroform/n-heptane/ethanol (10:10:1) as the eluant, care is taken that the eluate remains shielded from daylight. The uniform fractions are combined and evaporated, and there is obtained 2-(4-bromobutyl)-5-chloro-3-phenylisoindole-1-carboxylic acid ethyl ester as an oil, which has to be employed in the next stage as quickly as possible.

EXAMPLE 10

Preparation of 5-chloro-2-[2-(diethylamino)ethyl]-3-phenylisoindole-1-carboxylic acid methylamide According to the procedure described in Example 1, 28.5 g. of 5-chloro-3-phenylisoindole-1-carboxylic acid methylamide are treated with 34.5 g. of 2-diethylaminoethyl chloride hydrochloride. The mixture is heated at 70° C. for 5 hours, then cooled and poured into 4 liters of ice-water. After the addition of 200 g. of sodium chloride, the separated product is extracted with methylene chloride. The organic phase is washed with a saturated solution of sodium chloride, dried over sodium sulfate and concentrated to dryness under reduced pressure. The residue is digested with ether, removed by filtration and washed with ether, and there is obtained a first portion of crude 5-chloro-2-[2-(diethylamino)ethyl]-3-phenylisoindole-1-carboxylic acid methylamide having a melting point of 187°–190° C. The ethereal filtrate is extracted with 1-N sulfuric acid and the acidic extract is made alkaline at 0°–5° C. with concentrated ammonia solution. Then, the separated oil is extracted with methylene chloride and the solution dried over sodium sulfate. After evaporation, there is obtained an oil which crystallizes from ether, and is obtained as a second portion of reaction product; melting point 187°–190° C. Both portions of the reaction product are recrystallized together from ethanol, and 5-chloro-2-[2-diethylamino)ethyl]-3-phenylisoindole-1-carboxylic acid methylamide is obtained in the form of colorless needles having a melting point of 190°–192° C.

EXAMPLE 11

Preparation of 5-chloro-2-[2-(diethylamino)ethyl]-3-phenylisoindole-1-carboxylic acid ethyl ester hydrochloride A solution of 5.2 g. of 2-diethylaminoethyl chloride hydrochloride in 35 ml. of dimethylsulfoxide is treated with 8.3 g. of finely ground dry potassium carbonate and stirred at room temperature for 15 minutes. Then, there are added thereto 3.0 g. of 5-chloro-3-phenylisoindole-1-carboxylic acid ethyl ester; the mixture is stirred intensively for 18 hours under an atmosphere of nitrogen at room temperature and subsequently poured onto 80 ml. of ice-water. After the addition of 5 g. of sodium chloride, the separated oil is immediately extracted with ether, and the extract concentrated to about 30 ml. and treated with 30 ml. of 0.5–N hydrochloric acid. The mixture is thoroughly shaken and cooled in an ice-bath. The crystallized hydrochloride is isolated and purified in an analogous manner to that given in Example 1, and there is obtained 5-chloro-2-[2-(diethylamino)ethyl]-3-phenylisoindole-1-carboxylic acid ethyl ester hydrochloride having a melting point of 248°–250° C. (decomposition).

EXAMPLE 12

Preparation of 2-[2-(diethylamino)ethyl]-3-(α,α,α-trifluoro-m-tolyl)-isoindole-1-carboxylic acid ethyl ester hydrochloride In a manner analogous to that described in Example 1, from 3.33 g. of 3-(α,α,α-trifluoro-m-tolyl)-isoindole-1-carboxylic acid ethyl ester and 3.45 g. of 2-diethylaminoethyl chloride hydrochloride there is obtained a solid crude product which, after recrystallization from methylene chloride/ether, yields 2-[2-(diethylamino)ethyl]-3-(α,α,α-trifluoro-m-tolyl)-isoindole-1-carboxylic acid ethyl ester hydrochloride having a melting point of 234°–236° C. (decomposition).

The starting material can be prepared as follows:

A solution of 15.2 g. of 1,3-dihydro-5-(α,α,α-trifluoro-m-tolyl)-2H-1,4-benzodiazepin-2-one in 360ml. of acetone is treated with 7.5 ml. of dimethylsulfate and 45 g. of finely triturated, dry potassium carbonate and stirred intensively at room temperature for 15 hours. The mixture is then poured into 400 ml. of ice-water, the acetone is evaporated under reduced pressure and the separated oil extracted with methylene chloride. The extract is washed with water, dried over sodium sulfate and evaporated to dryness. The resulting oil crystallizes on trituration with hexane, and there is obtained 1,3-dihydro-1-methyl-5-($\alpha,\alpha,\alpha$-trifluoro-m-tolyl)-2H-1,4-benzodiazepin-2-one having a melting point of 117°–119° C., which can be employed in the next stage without further purification. A sample for analysis is obtained by crystallization from ethanol; melting point 121°–122° C.

According to the procedure described in Example 1, 1,3-dihydro-1-methyl-5-($\alpha,\alpha,\alpha$-trifluoro-m-tolyl)-2H-1,4-benzodiazepin-2-one is reacted with diethylcarbonate in the presence of sodium hydride, and there is obtained 3-($\alpha,\alpha,\alpha$-trifluoro-m-tolyl)-isoindole-1-carboxylic acid ethyl ester, having a melting point of 155°–157° C. Recrystallization from ethanol does not increase the melting point.

EXAMPLE 13

Preparation of
5-chloro-2-[2-(diethylamino)-ethyl]-3-phenylisoindole-1-carboxylic acid ethyl ester hydrochloride A solution of 0.84 g. of 5-chloro-2-{2-[(methylsulfonyl)oxy]ethyl}-3-phenylisoindole-1-carboxylic acid ethyl ester in 5 ml. of dimethylsulfoxide is treated with 5 ml. of diethylamine and boiled at reflux for 17 hours under exclusion of light. The excess diethylamine is then evaporated under reduced pressure and the resulting solution poured into 50 ml. of ice-water. After the addition of 3 g. of sodium chloride, the separated, thick oil is extracted with methylene chloride. The organic phase is washed with a saturated solution of sodium chloride, dried over sodium sulfate and concentrated to dryness under reduced pressure. The oily residue is dissolved in 15 ml. of acetone, treated with 10 ml. of 0.5-N hydrochloric acid and the mixture is thoroughly shaken. After cooling in an ice-bath, the crystallized hydrochloride is isolated and purified in a manner analogous to that described in Example 1, and there is obtained 5-chloro-2-[2-(diethylamino)-ethyl]-3-phenylisoindole-1-carboxylic acid ethyl ester hydrochloride; melting point 248°–250° C. (decomposition).

The starting material can be prepared as follows:

A solution of 30.0 g. of 5-chloro-3-phenylisoindole-1-carboxylic acid ethyl ester in 300 ml. of dimethylsulfoxide is treated with 66.8 g. of bromoacetic acid ethyl ester and 27.6 g. of finely triturated, dry potassium carbonate and intensively stirred at room temperature for 17 hours. The mixture is poured into 750 ml. of ice-water and the separated product, after the addition of 50 g. of sodium chloride, is removed by filtration under suction, washed with water and then dissolved in methylene chloride. The aqueous layer is separated, the organic phase dried over sodium sulfate, filtered and concentrated to dryness. The resulting oil crystallizes on trituration with ether and pentane, and there is obtained 1-ethoxycarbonyl-5-chloro-3-phenylisoindole-2-acetic acid ethyl ester; melting point 100°–101° C. Recrystallization from ethanol increases the melting point to 103°–104° C.

A suspension of 19.5 g. of 1-ethoxycarbonyl-5-chloro-3-phenylisoindole-2-acetic acid ethyl ester in 150 ml. of ethanol is treated with 60 ml. of 1.0-N sodium hydroxide and boiled at reflux for 30 minutes. After allowing the mixture to stand for 2 hours in an ice-bath, the crystallized sodium salt is removed by filtration under vacuum, washed with ethanol and then dissolved in a mixture of 400 ml. of ethanol and 250 ml. of water. The obtained solution is acidified with 160 ml. of 0.5-N hydrochloric acid with stirring at 40°–45° C. and then left to stand in an ice-bath for 2 hours. The separated acid is removed by filtration under vacuum, washed with water and then dissolved in 750 ml. of methylene chloride. The aqueous layer is separated, the organic phase dried over sodium sulfate and concentrated to about 200 ml. Then, the crystallized colorless acid is removed by filtration under suction and washed with a small amount of methylene chloride, and there is obtained 1-ethoxycarbonyl-5-chloro-3-phenylisoindole-2-acetic acid; melting point 217°–220° C. (decomposition).

A solution of 10.8 g. of 1-ethoxycarbonyl-5-chloro-3-phenylisoindole-2-acetic acid in 100 ml. of tetrahydrofuran is added dropwise under argon at 15°–20° C. to 72 ml. of a 1-M solution of borane in tetrahydrofuran. After stirring at room temperature for 60 hours, the clear solution is treated at 15°–20° C. with 30 ml. of ethanol and evaporated to dryness under reduced pressure. The solid residue is dissolved in methylene chloride and the obtained solution washed with a 5% sodium bicarbonate solution and then with water. The solution is dried over sodium sulfate, evaporated and the solid crude product obtained chromatographed on 700 g. of silica gel with methylene chloride/ethyl acetate (4:1) as the eluant. The uniform fractions yield 5-chloro-2-(2-hydroxyethyl)-3-phenylisoindole-1-carboxylic acid ethyl ester; melting point 114°–116° C. Recrystallization from ether/pentane does not increase the melting point.

A solution of 3.4 g. of 5-chloro-2-(2-hydroxyethyl)-3-phenylisoindole-1-carboxylic acid ethyl ester and 3.4 ml. of triethylamine in 60 ml. of methylene chloride is treated dropwise at 15°–20° C. with 1.6 ml. of methane sulfochloride. The mixture is subsequently left standing for 30 minutes at room temperature, then diluted with methylene chloride to three times the volume. The solution is washed successively with water, 0.5-N hydrochloric acid, 5% sodium bicarbonate solution and again with water. After drying over sodium sulfate and evaporation of the solution, there is obtained 5-chloro-2-{2-[(methylsulfonyl)oxy]ethyl}-3-phenylisoindole-1-carboxylic acid ethyl ester; melting point 125°–127° C. Recrystallization from methylene chloride/hexane does not increase the melting point.

EXAMPLE 14

Preparation of
5-chloro-2-[2-(diethylamino)ethyl]-3-phenylisoindole-1-carboxylic acid ethyl ester hydrochloride A solution of 0.82 g. of 5-chloro-2-[(diethylcarbamoyl)methyl]-3-phenylisoindole-1-carboxylic acid ethyl ester in 5 ml. of tetrahydrofuran is added dropwise under argon at room temperature to 3 ml. of a 1-M solution of borane in tetrahydrofuran. Subsequently, the mixture is boiled at reflux for 4 hours and then treated at 15°–20° C. with 0.8 ml. of 6-N hydrochloric acid. Then, the tetrahydrofuran is removed by distillation at atmospheric pressure. The residue is partitioned between 3 ml. of water and 5 ml. of ether. After cooling in an ice-bath, the crystallized hydrochloride is isolated and purified in a manner analogous to that described in Example 1, and there is obtained 5-chloro-2-[2-(diethylamino)ethyl]-3-phenylisoindole-1-carboxylic acid ethyl ester hydrochloride; melting point 248°–250° C. (decomposition).

The starting material can be prepared as follows:

A solution of 15.0 g. of 5-chloro-3-phenylisoindole-1-carboxylic acid ethyl ester in 250 ml. of hexamethylphosphoric triamide is treated under nitrogen at 5° C. with 0.055 mol. of sodium hydride (2.5 g. of a 55% dispersion in mineral oil) and then stirred at the same temperature for 15 minutes. At 5°–10° C. a solution of 15 g. of N,N-diethylchloroacetamide in 40 ml. of ethanol is added thereto and the mixture stirred for 30 minutes at room temperature and subsequently heated for 4 hours at 80° C. The mixture is cooled and poured into 2.5 liters of ice-water. After the addition of 150 g. of sodium chloride, the separated product is removed by filtration under suction, washed with water and then dissolved in methylene chloride. The aqueous layer is separated, the organic phase dried over sodium sulfate, filtered and evaporated to dryness. The residue is triturated with 100 ml. of ether, the unreacted starting material crystallizes out. The latter is removed by filtration under vacuum and washed with ether. The ethereal filtrate is evaporated to dryness. The oily residue is cooled and triturated with ether, crystals being obtained. Recrystallization from ethanol yields 5-chloro-2-[(diethylcarbamoyl)methyl]-3-phenylisoindole-1-carboxylic acid ethyl ester; melting point 118°–120° C.

EXAMPLE 15

Preparation of
2-(2-aminoethyl)-5-chloro-3-phenylisoindole-1-carboxylic acid ethyl ester hydrobromide 4.8 G. of 2-{2-[(benzyloxycarbonyl)amino]ethyl}-5-chloro-3-phenylisoindole-1-carboxylic acid ethyl ester are dissolved in 10 ml. of glacial acetic acid; 15 ml. of a solution of 33% hydrobromic acid in glacial acetic acid are added. The mixture is left to stand for 2 hours at room temperature with occasional shaking and then poured into 150 ml. of ether. The precipitated crystals are removed by filtration under suction and washed with ether. Recrystallization from ethanol yields 2-(2-aminoethyl)-5-chloro-3-phenylisoindole-1-carboxylic acid ethyl ester hydrobromide; melting point 230°–234° C. (decomposition).

In order to obtain the free base, the hydrobromide obtained according to the previous paragraph is treated with 2-N sodium carbonate in the presence of ether. The ethereal extract, shielded from light, is washed with water, dried over sodium sulfate and evaporated. The residue crystallizes on trituration with ether. Recrystallization from ether/hexane yields almost colorless crystals of 2-(2-aminoethyl)-5-chloro-3-phenylisoindole-1-carboxylic acid ethyl ester; melting point 84°–86° C.

The starting material can be prepared as follows:

15.0 G. of 5-chloro-3-phenylisoindole-1-carboxylic acid ethyl ester are reacted with 25.8 g. of 2-[(benzyloxycarbonyl)amino]ethyl bromide in a manner analogous to that described in Example 14. Thereafter, there is obtained an oily crude product, which is chromatographed on 250 g. of silica gel with methylene chloride/ethyl acetate (4:1) as the eluant. From the uniform fractions there is obtained 2{2-[(benzyloxycarbonyl)amino]ethyl}-5-chloro-3-phenylisoindole-1-carboxylic acid ethyl ester; melting point 102°–104° C. Recrystallization from ethanol increases the melting point to 140°–105° C.

EXAMPLE 16

Preparation of
5-chloro-2-[2-(dimethylamino)ethyl]-3-phenylisoindole-1-carboxylic acid ethyl ester hydrochloride A solution of 0.35 g. of 2-(2-aminoethyl)-5-chloro-3-phenylisoindole-1-carboxylic acid ethyl ester in 3 ml. of dimethylformamide is treated under nitrogen with 0.25 ml. of a 38% solution of formaldehyde in water and 0.17 ml. of an 85% solution of formic acid in water. The mixture is then heated for 90 minutes at 120° C., cooled and poured into 20 g. of ice-water. The pH value is adjusted to 8 with 2-N sodium hydroxide and the precipitated product immediately extracted with methylene chloride. The organic extract is washed with water, dried and treated with ethereal hydrochloric acid in excess. After concentration, the solid residue is recrystallized from methylene chloride/ether, and there is obtained 5-chloro-2-[2-(dimethylamino)ethyl]-3-phenylisoindole-1-carboxylic acid ethyl ester hydrochloride, having a melting point of 192°–194° C.

EXAMPLE 17

Preparation of
2-[3-(butylmethylamino)propyl]-5-chloro-3-phenylisoindole-1-carboxylic acid ethyl ester hydrochloride A solution of 4.36 g. of 5-chloro-2-{3-[(methylsulfonyl)oxy]propyl}-3-phenylisoindole-1-carboxylic acid ethyl ester in 40 ml. of acetone is treated with 10 ml. of N-methylbutylamine and boiled at reflux for 5 hours. The mixture is then concentrated to dryness under reduced pressure and the residue partitioned between 50 ml. of water and 50 ml. of ether. The ethereal phase is treated with 30 ml. of 0.5-N hydrochloric acid and the mixture thoroughly shaken. After cooling in an ice-bath, the crystallized hydrochloride is removed by filtration under vacuum, dried and recrystallized from methylene chloride/ether, and there is obtained 2-[3-(butylmethylamino)propyl]-5-chloro-3-phenylisoindole-1-carboxylic acid ethyl ester hydrochloride having a melting point of 98°–101° C. (decomposition).

The starting material can be prepared as follows:

15.0 G. of 5-chloro-3-phenylisoindole-1-carboxylic acid ethyl ester are reacted with 22.3 g. of 3-bromopropyl tetrahydropyran-2-yl ether in a manner analogous to that described in Example 14. The reaction yields an oily tetrahydropyranyl derivative, which for hydrolysis is boiled at reflux with 600 ml. of ethanol, 40 ml. of water and 10 ml. of concentrated hydrochloric acid for 3 hours. The mixture is then evaporated to dryness under reduced pressure, and the residue taken up in methylene chloride, washed with water and dried over sodium sulfate. After concentration, the resulting oil is chromatographed on 350 g. of silica gel with methylene chloride/ethyl acetate (4:1) as the eluant. From the uniform fractions, there is obtained 5-chloro-2-(3-hydroxypropyl)-3-phenylisoindole-1-carboxylic acid ethyl ester; melting point 94°–96° C. Recrystallization from ether/hexane does not increase the melting point.

A solution of 10.8 g. of 5-chloro-2-(3-hydroxypropyl)-3-phenylisoindole-1-carboxylic acid ethyl ester and 10.2 ml. of triethylamine in 150 ml. of methylene chloride is treated dropwise at 15°–20° C. with a solution of 4.8 ml. of methanesulfochloride in 30 ml. of methylene chloride. The mixture is subsequently left to stand at room temperature for 30 minutes, then diluted with methylene chloride to twice the volume. The thus obtained solution is washed successively with water, 0.5-N hydrochloric acid, 5% sodium bicarbonate solution and again with water. After drying and evaporation of the solution, there is obtained 5-chloro-2-{3-[(methylsulfonyl)oxy]propyl}-3-phenylisoindole-1-carboxylic acid ethyl ester having a melting point of 89°–91° C.; this is employed in the next stage without additional purification. A sample for analysis is obtained by crystallization from ether/hexane; melting point 91°–92° C.

In a manner analogous to that described above, the following isoindole derivatives can be prepared:

| Amine | Isoindole derivative |
|---|---|
| diethanolamine | 2-{3-[bis(2-hydroxyethyl)amino]-propyl}-5-chloro-3-phenylisoindole-1-carboxylic acid ethyl ester hydrochloride; melting point 205°–207° C. (decomposition) |
| N-methylpiperidine | 5-chloro-2-[3-(4-methyl-1-piperazinyl)-propyl]-3-phenylisoindole-1-carboxylic acid ethyl ester dihydrochloride; melting point 260°–265° C. (decomposition) |
| ethylamine | 2-[3-(ethylamino)propyl]-5-chloro-3-phenylisoindole-1-carboxylic acid ethyl ester hydrochloride; melting point 182°–184° C. (decomposition) |

EXAMPLE 18

Preparation of 5-chloro-2-[3-(diethylamino)propyl]-3-phenylisoindole-1-carboxylic acid ethyl ester hydrochloride A solution of 0.84 g. of 2-[3-(N-ethylacetamido)propyl]-5-chloro-3-phenylisoindole-1-carboxylic acid ethyl ester in 5 ml. of tetrahydrofuran is added dropwise under argon at room temperature to 3 ml. of a 1-M solution of borane in tetrahydrofuran. Subsequently, the mixture is heated at reflux for 4 hours, then treated at 15°–20° C. with 0.8 ml. of 6-N hydrochloric acid and the tetrahydrofuran is removed by distillation at atmospheric pressure. The residue is partitioned between 3 ml. of water and 5 ml. of ether and cooled in an ice-bath. The crystallized hydrochloride is isolated and purified in a manner analogous to that described in Example 5, and there is obtained 5-chloro-2-[3-(diethylamino)-propyl]-3-phenylisoindole-1-carboxylic acid ethyl ester hydrochloride having a melting point of 203°–206° C. (decomposition).

The starting material can be prepared as follows:
2.1 G. of 2-[3-(ethylamino)propyl]-5-chloro-3-phenylisoindole-1-carboxylic acid ethyl ester hydrochloride is treated with 10 ml. of 1-N sodium hydroxide and the liberated base extracted with ether. After evaporation of the extracts, the oily residue is dissolved in a mixture of 10 ml. of benzene and 2 ml. of acetic anhydride and the solution boiled at reflux for 2 hours. Thereafter, there are added 5 ml. of ethanol, the mixture is boiled for an additional 15 minutes and concentrated to dryness under reduced pressure. The oily residue is dissolved in methylene chloride and the obtained solution washed with a 5% sodium bicarbonate solution and then with water. The solution is dried over sodium sulfate, evaporated and the resulting oil chromatographed on 100 g. of silica gel with ethyl acetate as the eluant. The uniform fractions yield 2-[3-(N-ethylacetamido)propyl]-5-chloro-3-phenylisoindole-1-carboxylic acid ethyl ester; melting point 102°–104° C. Recrystallization from ether does not increase the melting point.

EXAMPLE 19

Preparation of 3-(p-chlorophenyl)-2-[2-(diethylamino)ethyl]isoindole-1-carboxylic acid ethyl ester hydrochloride A mixture of 0.83 g. of formic acid and 1.05 g. of 2-diethylaminoethylamine is treated at room temperature with 0.95 g. of [o-(p-chlorobenzoyl)phenyl]-glyoxylic acid ethyl ester and subsequently stirred at 140° C. for 2 hours. After cooling, the obtained solution is made alkaline with 2-N ammonium hydroxide with addition of ice and extracted with ether. The extract, shielded from daylight, is washed with water, dried over sodium sulfate, concentrated and chromatographed on 70 g. of silica gel with ether as the eluant. The homogeneous fractions are combined, concentrated to a volume of 15–20 ml. and treated with ethereal hydrochloric acid. The crystallized hydrochloride is removed by filtration and washed with ether, and there is obtained 3-(p-chlorophenyl)-2-[2-(diethylamino)ethyl]isoindole-1-carboxylic acid ethyl ester hydrochloride; melting point 202°–204° C. (decomposition). Recrystallization from methylene chloride/ether does not increase the melting point.

The starting material can be prepared as follows:
A suspension of 4.9 g. of o-(p-chlorobenzoyl)-benzaldehyde in 28 ml. of water is treated with 7.6 g. of sodium pyrosulfite and heated to 80° C. until a clear solution results (2–4 minutes). The mixture is immediately cooled in an ice-bath and there is added dropwise thereto at 10°–15° C. a solution of 5.2 g. of potassium cyanide in 8 ml. of water, a thick oil separating. After stirring at 0°–5° C. for 15 minutes, the aqueous phase is separated by decantation and the honey-like residue digested twice with ice-water. The thus obtained crude cyanohydrin of o-(p-chlorobenzoyl)benzaldehyde is immediately treated in an ice-bath with 15 ml. of concentrated hydrochloric acid and ground well with a glass rod. The mass becomes orange and solidifies after a short time. The mixture is subsequently stirred for 3 hours at room temperature, water is added to twice the volume, and the mixture is stirred for an additional 0.5 hour at room temperature and then extracted with methylene chloride. The organic phase is washed successively with water, a sodium bicarbonate solution and a saturated solution of sodium chloride in water. After drying over sodium sulfate and concentration under reduced pressure, there is obtained a yellow residue which is chromatographed on 150 g. of silica gel with methylene chloride as the eluant. The homogeneous fractions are combined and triturated with a small amount of hexane, and there is obtained 3-(p-chlorophenyl)-1-cyano-isobenzofuran in the form of yellow crystals; melting point 128°–130° C. Crystallization from ethanol does not increase the melting point.

A suspension of 5 g. of 3-(p-chlorophenyl)-1-cyano-isobenzofuran in 135 ml. of ether is treated with 50 ml. of a 20% solution of hydrochloric acid in ethanol and stirred at room temperature for 48 hours. The crystallized orange iminoether hydrochloride is removed by filtration under suction, washed with ether and hydrolyzed by boiling for 90 minutes with 300 ml. of water. After cooling, the separated oil is extracted with methylene chloride, the extract washed with a sodium bicarbonate solution and dried over sodium sulfate. By concentration in vacuo, there is obtained a yellow oil which is chromatographed on 150 g. of silica gel with methylene chloride as the eluant. The homogeneous fractions are combined, concentrated, and the solid residue is recrystallized from ether/hexane, 3-(p-chlorophenyl)-isobenzofuran-1-carboxylic acid ethyl ester being obtained in the form of fibrous crystals having a melting point of 99°–101° C. 11.5 G. of cerium (IV) ammonium nitrate are dissolved in 20 ml. of water and 20 ml. of glacial acetic acid. Thereafter, there are added 3.0 g. of 3-(p-chlorophenyl)-isobenzofuran-1-carboxylic acid ethyl ester and the mixture is boiled for 2–3 minutes until the color of the solution obtained changes from orange to light-yellow. After cooling, there are added 150 ml. of ice-water and the mixture is stirred for 1 hour in an ice-bath. The product which first separates as an oil solidifies. The solid is separated by decantation of the aqueous solution and is dissolved in ether. The ethereal solution is washed with 2-N sodium carbonate and water, dried over sodium sulfate and evaporated. After crystalization of the residue from ethanol, there is obtained [o-(p-chlorobenzoyl)-phenyl]glyoxylic acid ethyl ester in the form of colorless crystals having a melting point of 79°–81° C.

EXAMPLE 20

Preparation of
5-chloro-2-[2-(diethylamino)ethyl]-3-phenylisoindole-1-carboxylic acid ethyl ester hydrochloride In a manner analogous to that described in Example 19, from 0.95 g. of o-benzoyl-p-chloro-phenylglyoxylic acid ethyl ester, 1.05 g. of 2-diethylaminoethylamine and 0.83 g. of formic acid, there is obtained 5-chloro-2-[2-(diethylamino)ethyl]-3-phenylisoindole-1-carboxylic acid ethyl ester hydrochloride; melting point 248°–250° C. (decomposition).

The starting material can be prepared from o-benzoyl-p-chlorobenzaldehyde in a manner analogous to that described in Example 19. The following compounds are obtained as intermediates:

5-chloro-1-cyano-3-phenylisobenzofuran; yellow crystals (recrystallization from ethanol); melting point 128°–130° C.;
5-chloro-3-phenylisobenzofuran-1-carboxylic acid ethyl ester; yellow crystals (recrystallization from ethanol); melting point 78°–80° C.;
o-benzoyl-p-chloro-phenylglyoxylic acid ethyl ester as a light-yellow thick oil after chromatography on silica gel with methylene chloride as the eluant.

EXAMPLE 21

Preparation of
5-chloro-2-[2-(diethylamino)ethyl]-3-phenylisoindole-1-carboxylic acid ethyl ester hydrochloride A solution of 3.5 g. of 2-diethylaminoethylamine in 10 ml. of methanol is treated with 2 ml. of 5-N methanolic hydrochloric acid. Then, there are added successively under argon at 20°–25° C. a solution of 1.6 g. of o-benzoyl-p-chlorophenylglyoxylic acid ethyl ester in 5 ml. of methanol and 0.2 g. of sodium cyanoborohydride and the mixture is stirred for an additional 7 hours at room temperature. While cooling with ice, the mixture is made acidic with concentrated hydrochloric acid, stirred for an additional 0.5 hour at room temperature and evaporated to dryness under reduced pressure. The residue is made alkaline with 1-N sodium hydroxide with addition of ice and extracted with 50 ml. of ether. The ethereal extract is treated with 20 ml. of 0.5-N hydrochloric acid, and the mixture shaken thoroughly. After cooling in an ice-bath, the crystallized hydrochloride is isolated and purified in a manner analogous to that described in Example 1, and there is obtained 5-chloro-2-[2-(diethylamino)ethyl]-3-phenylisoindole-1-carboxylic acid ethyl ester hydrochloride; melting point 248°–250° C. (decomposition).

EXAMPLE 22

Preparation of
5-chloro-2-[2-(diethylamino)ethyl]-3-phenylisoindole-1-carboxylic acid dimethylamide cyclohexanesulfamate According to the procedure described in Example 21, 1.6 g. of o-benzoyl-p-chloro-phenylglyoxylic acid dimethylamide are reacted with 3.5 g. of 2-diethylaminoethylamine and 0.2 g. of sodium cyanoborohydride. The ether extract from the free base is concentrated to dryness and the oily residue chromatographed on 80 g. of aluminum oxide [neutral; Brockmann activity I] with methylene chloride/ethyl acetate (4:1) as the eluant. The homogeneous fractions are combined and evaporated. The resulting oil is dissolved in 10 ml. of acetone and treated with 0.9 g. of N-cyclohexylsulfaminic acid. After standing overnight in a refrigerator, the crystallized, almost colorless salt is removed by filtration under vacuum, washed with a small amount of ether and dried in a dessicator, and there is obtained 5-chloro-2-[2-(diethylamino)ethyl]-3-phenylisoindole-1-carboxylic acid dimethylamide cyclohexanesulfamate; melting point 107°–109° C.

The starting material can be prepared as follows:

A suspension of 9.0 g. of 5-chloro-2-methyl-3-phenylisoindole-1-carboxylic acid methylamide in 120 ml. of dimethylformamide is treated under argon at 0° C. with 5.0 g. of potassium tert. butylate and then stirred in an ice-bath for 30 minutes. At 0°–5° C. there are added 8 ml. of methyl iodide in one batch, the mixture is subsequently stirred for 2 hours at room temperature and poured onto 2 liters of ice-water. After the addition of 100 g. of sodium chloride, the separated oil is extracted with methylene chloride. The organic phase is washed with a solution of sodium chloride, dried over sodium sulfate and concentrated to dryness under reduced pressure. The oily residue is dissolved in 200 ml. of hot hexane. The solution obtained is cooled in an ice-bath, colorless crystals separating, and there is obtained 5-chloro-2-methyl-3-phenylisoindole-1-carboxylic acid dimethylamide having a melting point of 86°–88° C.

23 G. of cerium (IV) ammonium nitrate are dissolved in 80 ml. of glacial acetic acid/water (1:1) and 6.25 g. of 5-chloro-2-methyl-3-phenylisoindole-1-carboxylic acid dimethylamide are added thereto. The mixture is heated at reflux for 2 minutes, cooled in an ice-bath and then 200 ml. of ice-water are added. The mixture is stirred for 1 hour at 0°–5° C. and the oily precipitate is separated by decantation of the aqueous solution and taken up in methylene chloride. The organic solution is washed with 2-N sodium carbonate solution and with water, dried over sodium sulfate and evaporated. The residue is purified by chromatography on 300 g. of silica gel with methylene chloride/ethyl acetate (4:1) as the eluant. The homogeneous fractions are crystallized from hexane to give o-benzoyl-p-chloro-phenylglyoxylic acid dimethylamide having a melting point of 88°–90° C.

EXAMPLE 23

Preparation of
5-chloro-3-(3,4-dichlorophenyl)-2-[2-(diethylamino)-ethyl]-isoindole-1-carboxylic acid ethyl ester hydrochloride In a manner analogous to that described in Example 4, from 7-chloro-5-(3,4-dichlorophenyl)-1,3-dihydro-1-methyl-2H-1,4-benzodiazepin-2-one, diethyl carbonate and 2-diethylaminoethyl chloride hydrochloride, there is obtained a solid crude product which, after recrystallization from methylene chloride/ether, gives 5-chloro-3-(3,4-dichlorophenyl)-2-[2-(diethylamino)-ethyl]isoindole-1-carboxylic acid ethyl ester hydrochloride having a melting point of 227°–229° C. (decomposition).

EXAMPLE 24

Preparation of
2-[2-(diethylamino)ethyl]-3-phenyl-5-trifluoromethyl-isoindole-1-carboxylic acid ethyl ester hydrochloride In a manner analogous to that described in Example 4, from 1,3-dihydro-1-methyl-5-phenyl-7-trifluoromethyl-2H-1,4-benzodiazepin-2-one, diethyl carbonate and 2-diethylaminoethyl chloride hydrochloride, there is obtained a solid crude product which, after recrystallization from methylene chloride/ether, gives 2-[2-(diethylamino)ethyl]-3-phenyl-5-trifluoromethyl-isoindole-1-carboxylic acid ethyl ester hydrochloride having a melting point of 225°–227° C. (decomposition).

EXAMPLE 25

Preparation of
5-chloro-2-[2-(diethylamino)ethyl]-3-phenylisoindole-1-carboxylic acid benzylamide In a manner analogous to that described in Example 10, by the reaction of 18.0 g. of 5-chloro-3-phenylisoindole-1-carboxylic acid benzylamide with 17.2 g. of 2-diethylaminoethyl chloride hydrochloride, there is obtained 5-chloro-2-[2-(diethylamino)ethyl]-3-phenylisoindole-1-carboxylic acid benzylamide, which, after recrystallization from ethanol, has a melting point of 152°–153° C.

The starting material can be prepared as follows:
A solution of 36.1 g. of 1-benzyl-7-chloro-1,3-dihydro-5-phenyl-2H-1,4-benzodiazepin-2-one in 300 ml. of dimethylformamide is treated under an atmosphere of argon at room temperature with 0.11 mol. of sodium hydride (4.8 g. of a 55% dispersion in mineral oil). The mixture is first heated to 60° C. over a period of about 30 minutes, and then stirred for 1 hour at this temperature for an additional 1 hour at 70° C. After cooling, 10 ml. of water are added dropwise and the mixture is poured into 3 liters of ice-water. After the addition of 100 g. of sodium chloride, the separated product is extracted with methylene chloride. The organic phase is washed with a saturated solution of sodium chloride, dried over sodium sulfate and concentrated to dryness. The resulting oily residue is chromatographed on 1000 g. of silica gel with methylene chloride/ethyl acetate (4:1) as the eluant. The homogeneous fractions are combined, evaporated and triturated with a small amount of ether, and there is obtained 5-chloro-3-phenylisoindole-1-carboxylic acid benzylamide in the form of fibrous, greenish crystals; melting point 202°–204° C. (decomposition). Recrystallization from chloroform does not increase the melting point.

In a manner analogous to that described above, the following isoindole derivatives can be prepared:

| Starting material | Isoindole derivative |
| --- | --- |
| 5-chloro-3-phenylisoindole-1-carboxylic acid ethylamide; melting point 237°–240° C. (decomposition) | 5-chloro-2-[2-(diethylamino)ethyl]-3-phenylisoindole-1-carboxylic acid ethylamide; melting point 158°–160° C. |
| 5-chloro-3-phenylisoindole-1-carboxylic acid isobutylamide; melting point 205°–207° C. (decomposition) | 5-chloro-2-[2-(diethylamino)ethyl]-3-phenylisoindole-1-carboxylic acid isobutylamide; melting point 161°–163° C. |
| 5-chloro-3-phenylisoindole-1-carboxylic acid (2-ethoxyethyl)-amide; melting point 145°–147° C. | 5-chloro-2-[2-(diethylamino)ethyl]-3-phenylisoindole-1-carboxylic acid (2-ethoxyethyl)amide; melting point 116°–118° C. |
| 5-chloro-3-phenylisoindole-1-carboxylic acid cyclohexylamide; melting point 211°–213° C. | 5-chloro-2-[2-(diethylamino)ethyl]-3-phenylisoindole-1-carboxylic acid cyclohexylamide; melting point 193°–194° C. |

EXAMPLE 26

Preparation of
2-(5-butylmethylamino-3,3-dimethylpentyl)-5-chloro-3-phenylisoindole-1-carboxylic acid ethyl ester hydrochloride A solution of 8.4 g. of silver toluene-4-sulfonate in 80 ml. of acetonitrile is treated at room temperature with 9.5 g. of 2-(5-bromo-3,3-dimethylpentyl)-5-chloro-3-phenylisoindole-1-carboxylic acid ethyl ester and then heated to reflux with the exclusion of light for 3 hours. The mixture is then concentrated to dryness under reduced pressure and the residue boiled out for 2–3 minutes with 200 ml. of ethylene chloride. After cooling, the silver salts are removed by filtration and the filtrate is evaporated to dryness. The resulting oily tosylate is immediately dissolved in 80 ml. of acetone, treated with 20 ml. of N-butylmethylamine and heated at reflux with the exclusion of light for 17 hours. Then, the solution is filtered hot and immediately concentrated to dryness. The residue is partitioned between 150 ml. of ether and 100 ml. of water. The separated ethereal solution is treated with 60 ml. of 0.5-N hydrochloric acid and the mixture thoroughly shaken. After cooling in an ice-bath, the crystallized hydrochloride is removed by filtration under suction, washed with water and ether and then dissolved in 80 ml. of methylene chloride. The aqueous layer is separated, the organic phase dried over sodium sulfate, filtered and diluted with ether portionwise to four times the volume; 2-(5-butylmethylamino-3,3-dimethylpentyl)-5-chloro-3-phenylisoindole-1-carboxylic acid ethyl ester hydrochloride crystallizes out; melting point 197°–199° C. (decomposition). Recrystallization from methylene chloride/ether gives almost colorless crystals having a melting point 198°–200° C. (decomposition).

The starting material can be prepared as follows:

A solution of 24 g. of 5-chloro-3-phenylisoindole-1-carboxylic acid ethyl ester in 480 ml. of dimethylformamide is treated under argon at -10° C. With 0.16 mol. of sodium hydride (7.0 g. of a 55% dispersion in mineral oil) and then stirred in an ice-bath for 15 minutes. To this, 62 g. of 1,5-dibromo-3,3-dimethylpentane are added in one batch at -5° C., the mixture is then stirred for 1 hour at room temperature and subsequently heated for 18 hours at 60° C. After cooling, the mixture is poured into 4 liters of ice-water, 200 g. of sodium chloride are added, and the separated product is immediately extracted with methylene chloride. The organic phase, shielded from daylight, is washed with a saturated solution of sodium chloride, dried over sodium sulfate and concentrated to dryness under reduced pressure. The resulting oily residue is chromatographed on 1000 g. of silica gel with methylene chloride as the eluant, care being taken that the eluate is shielded from daylight. The homogeneous fractions are combined, evaporated, and the solid residue recrystallized from ethanol, and there is obtained 2-(5-bromo-3,3-dimethylpentyl)-5-chloro-3-phenylisoindole-1-carboxylic acid ethyl ester having a melting point of 87°–88° C.

EXAMPLE 27

Preparation of 5-chloro-2-[4-(isopropylamino)pentyl]-3-phenylisoindole-1-carboxylic acid ethyl ester hydrochloride A solution of 5.2 ml. of isopropylamine in 25 ml. of methanol is treated with 4 ml. of 5-N methanolic hydrochloric acid. To this there are added successively under an atmosphere of argon at 20°–25° C. 3.85 g. of 5-chloro-2-(4-oxopentyl)-3-phenylisoindole-1-carboxylic acid ethyl ester and 0.4 g. of sodium cyanoborohydride and the mixture is then stirred for 48 hours at room temperature. While cooling, the mixture is made acidic with concentrated hydrochloric acid, stirred for an additional 1 hour at room temperature and subsequently evaporated to dryness under reduced pressure. The residue is made alkaline with 1-N sodium hydroxide with addition of ice and is extracted with ether. The extract is dried over sodium sulfate, concentrated, and the oily residue chromatographed on 200 g. of silica gel with a mixture of ethyl acetate/tetrahydrofuran/triethylamine (40:10:1). The homogeneous fractions are combined, concentrated, dissolved in ether and treated with an excess of ethereal hydrochloric acid. The precipitated hydrochloride is removed by filtration and washed with ether. After recrystallization from acetone, there is obtained 5-chloro-2-[4-(isopropylamino)pentyl]-3-phenylisoindole-1-carboxylic acid ethyl ester hydrochloride having a melting point of 183°–185° C. (decomposition).

The starting material can be prepared as follows:

A solution of 24.0 g. of 5-chloro-3-phenylisoindole-1-carboxylic acid ethyl ester in 480 ml. of dimethylformamide is treated under an atmosphere of argon at -10° C. with 0.16 mol. of sodium hydride (7.2 g. of a 55% dispersion in mineral oil) and then stirred for an additional 30 minutes in an ice-bath. Thereafter, there are added at 0° C. 26.5 g. of 2-(3-chloropropyl)-2-methyl-1,3-dioxolane in one batch. The resulting mixture is then stirred for 1 hour at 20°–25° C. and subsequently heated for 2 hours at 140° C. The mixture is cooled and poured into 4 liters of ice-water. After the addition of 200 g. of sodium chloride, the separated product is removed by filtration under suction, washed with water and then dissolved in methylene chloride. The aqueous layer is separated, the organic phase dried over sodium sulfate, filtered and concentrated to dryness. The residue is triturated with 300 ml. of ethanol, and the unreacted starting material crystallizes out. The latter is removed by filtration under vacuum and washed with ether. The filtrate is concentrated to dryness and the resulting oily residue purified by chromatography on 300 g. of silica gel with chloroform as the eluant, and there is obtained 5-chloro-2-[4-(1,3-dioxolan-2-yl)pentyl]-3-phenylisoindole-1-carboxylic acid ethyl ester; melting point 100°–101° C.

A suspension of 8 g. of 5-chloro-2-[4-(1,3-dioxolan-2-yl)pentyl]-3-phenylisoindole-1-carboxylic acid ethyl ester in a mixture of 40 ml. of dioxane and 10 ml. of water is treated with 2 ml. of concentrated hydrochloric acid and then boiled at reflux for 3 hours. The solution obtained is concentrated to dryness under reduced pressure and the residue partitioned between water and methylene chloride. The organic phase is washed with a 2-N sodium carbonate solution and then with a saturated aqueous sodium chloride solution. After drying over sodium sulfate, the solvent is removed, and there is obtained 5-chloro-2-(4-oxophenyl)-3-phenylisoindole-1-carboxylic acid ethyl ester having a melting point of 93°–94° C. Crystallization from ether/hexane yields colorless crystals; melting point 94°–95° C.

EXAMPLE 28

Preparation of 5-chloro-2-{3-[bis(methoxyethyl)amino]propyl}-3-phenylisoindole-1-carboxylic acid ethyl ester hydrochloride A solution of 4.36 g. of 5-chloro-2-{3-[(methylsulfonyl)oxy]propyl}-3-phenylisoindole-1-carboxylic acid ethyl ester in 40 ml. of acetone is treated with 10 ml. of bis-(2-methoxyethyl)amine and boiled at reflux for 17 hours. The mixture is then concentrated to dryness under reduced pressure and the residue taken up in ether. After acidification with ethereal hydrochloric acid, the crystallized hydrochloride is removed by filtration under vacuum, dried and recrystallized from methylene chloride/ether, and there is obtained 5-chloro-2-{3-[bis(methoxyethyl)amino]proyl}-3-phenylisoindole-1-carboxylic acid ethyl ester hydrochloride; melting point 120°–122° C.

In a manner analogous to that described above, from 4.36 g. of 5-chloro-2-{3-[(methylsulfonyl)oxy]propyl}-3-phenylisoindole-1-carboxylic acid ethyl ester and 10 ml. of cyclohexylamine, there is obtained a crude hydrochloride which, after recrystallization from ethanol, gives 2-[3-(cyclohexylamino) propyl]-5-chloro-3-phenylisoindole-1-carboxylic acid ethyl ester hydrochloride having a melting point of 212°–214° C. (decomposition).

EXAMPLE 29

Preparation of 5-chloro-2-[3-(N-methylanilino)propyl]-3-phenylisoindole-1-carboxylic acid ethyl ester A solution of 4.36 g. of 5-chloro-2-{3-[(methylsulfonyl)oxy]propyl}-3-phenylisoindole-1-carboxylic acid ethyl ester in 25 ml. of hexamethylphosphoric acid triamide is treated with 25 ml. of N-methylaniline and heated at 80° C. for 24 hours. The mixture is then evaporated to dryness under reduced pressure, and the residue treated with 250 ml. of ice-water. The oily precipitate is taken up in methylene chloride and the extract washed with a saturated solution of sodium chloride, dried over sodium sulfate and concentrated to dryness. The resulting oil is purified by chromatography on 150 g. of aluminum oxide [neutral; Brockmann activity]. By elution with methylene chloride and evaporation of the solvent, there is obtained 5-chloro-2-[3-(N-methylanilino)propyl]-3-phenyl isoindole-1-carboxylic acid ethyl ester; melting point 108°–110° C. Crystallization from ether/hexane gives almost colorless crystals of the same melting point.

The following Examples illustrate pharmaceutical preparations containing the isoindole derivatives of the invention:

EXAMPLE A

Tablets of the following composition are prepared:

|  | Per Tablet |
|---|---|
| 5-chloro-2-[2-(diethylamino)ethyl]-3-phenylisoindole-1-carboxylic acid ethyl ester hydrochloride | 5.46 mg. |
| Lactose | 57.54 mg. |
| Maize starch | 54.00 mg. |
| Talc | 2.70 mg. |
| Magnesium stearate | 0.30 mg. |
| Total Weight | 120.00 mg. |

The isoindole derivative is carefully mixed with the lactose and a portion of the maize starch and passed through a sieve. A paste is prepared with the remaining maize starch and processed with the powder mixture to a granulate in a known manner. The granulate is then dried. After admixing the residual ingredients, tablets with a total weight of 120.0 mg. are pressed.

EXAMPLE B

Capsules of the following composition are prepared:

|  | Per Capsule |
|---|---|
| 5-chloro-2-[2-(diethylamino)ethyl]-3-phenylisoindole-1-carboxylic acid ethyl ester hydrochloride | 5.46 mg. |
| Lactose | 104.54 mg. |
| Maize starch | 20.00 mg. |
| Talc | 9.00 mg. |
| Magnesium stearate | 1.00 mg. |
| Total Weight | 140.00 mg. |

To prepare 10,000 capsules, the 10,000-fold amount of the above ingredients are made ready. 54.6 G. of isoindole derivative are mixed homogeneously with the same amount of lactose. The resulting mixture is then further diluted with 109.2 g. of lactose and again mixed homogeneously. The dilution process is continued until all the lactose is used up. Then, the maize starch, talc and magnesium stearate are added and homogeneously distributed in a suitable mixing machine. The finished mixture is filled on a capsule-filling machine into capsules each containing 140 mg.

I claim:

1. A compound of the formula

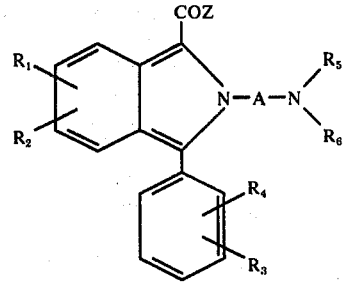

wherein A is alkylene containing 2–10 carbon atoms, Z is the group -OR or

R is alkyl, cycloalkyl, cycloalkylalkyl, alkoxyalkyl, allyl or aralkyl, $R_1$, $R_2$, $R_3$ and $R_4$, independently, are hydrogen, halogen, alkyl, alkoxy or trifluoromethyl, and $R_5$ and $R_6$, independently, are hydrogen, alkyl, cycloalkyl, cycloalkylalkyl, hydroxyalkyl, alkoxyalkyl, aryl or aralkyl, or $R_5$ and $R_6$, taken together, are —$(CH_2)_n$—, wherein n is an integer of 2-7, or $R_5$ and $R_6$, taken together with the nitrogen atom to which they are attached, are a 5-membered or 8-membered heterocyclic ring containing an oxygen atom or an additional nitrogen atom which may be substituted by alkyl or hydroxyalkyl, and $R_7$ and $R_8$, independently, are hydrogen, alkyl, cycloalkyl, cycloalkylalkyl, alkoxyalkyl or aralkyl, provided that at least one of $R_7$ and $R_8$ is other than hydrogen, or a pharmaceutically acceptable acid addition salt thereof.

2. A compound in accordance with claim 1, wherein Z is —OR.

3. A compound in accordance with claim 1, wherein Z is

4. A compound in accordance with claim 1, wherein $R_1$, $R_2$, $R_3$ and $R_4$, independently, are hydrogen, halogen, or trifluoromethyl.

5. A compound in accordance with claim 4, wherein $R_4$ is hydrogen, $R_1$ is chlorine, fluorine or trifluoromethyl, $R_2$ and $R_3$, independently, are hydrogen, chlorine or fluorine.

6. A compound in accordance with claim 5, wherein $R_5$ and $R_6$, independently, are alkyl.

7. A compound in accordance with claim 6, wherein $R_5$ and $R_6$, independently, are ethyl or isopropyl.

8. A compound in accordance with claim 4, wherein A is ethylene or trimethylene.

9. A compound in accordance with claim 1, wherein Z is —OR or —NHR$_7$.

10. A compound in accordance with claim 9, wherein R and R$_7$, independently, are alkyl.

11. A compound in accordance with claim 10, wherein R and R$_7$, independently, are ethyl or isopropyl.

12. A compound in accordance with claim 11, wherein R$_4$ is hydrogen, R$_1$ is chlorine, fluorine or trifluoromethyl, R$_2$ and R$_3$, independently, are hydrogen, chlorine or fluorine, R$_5$ and R$_6$, independently, are ethyl or isopropyl, and A is ethylene or trimethylene.

13. The compound in accordance with claim 2, 5-chloro-2-[2-(diethylamino)ethyl]-3-phenylisoindole-1-carboxylic acid ethyl ester.

14. The compound in accordance with claim 2, 5-chloro-2-[2-(dibutylamino)ethyl]-3-phenylisoindole-1-carboxylic acid ethyl ester.

15. The compound in accordance with claim 2, 5-chloro-2-[2-(diethylamino)ethyl]-3-phenylisoindole-1-carboxylic acid benzyl ester.

16. The compound in accordance with claim 2, 5-chloro-2-[2-(diethylamino)ethyl]-3-phenylisoindole-1-carboxylic acid isobutyl ester.

17. The compound in accordance with claim 2, 5-chloro-2-[2-(diethylamino)ethyl]-3-phenylisoindole-1-carboxylic acid allyl ester.

18. The compound in accordance with claim 2, 5-chloro-2-[3-(diethylamino)propyl]-3-phenylisoindole-1-carboxylic acid ethyl ester.

19. The compound in accordance with claim 2, 5-chloro-2-[2-diisopropylamino)ethyl]-3-phenylisoindole-1-carboxylic acid ethyl ester.

20. The compound in accordance with claim 2, 5-chloro-2-[2-(diethylamino)ethyl]-3-phenylisoindole-1-carboxylic acid isopropyl ester.

21. The compound in accordance with claim 2, 6-chloro-2-[2-(diethylamino)ethyl]-3-phenylisoindole-1-carboxylic acid ethyl ester.

22. The compound in accordance with claim 2, 5-chloro-3-(p-chlorophenyl)-2-[2-(diethylamino)ethyl]-isoindole-1-carboxylic acid ethyl ester.

23. The compound in accordance with claim 2, 5,7-dichloro-2-[2-(diethylamino)ethyl]-3-phenylisoindole-1-carboxylic acid ethyl ester.

24. The compound in accordance with claim 2, 5-chloro-2-[2-(diethylamino)ethyl]-3-(o-fuorophenyl)-isoindole-1-carboxylic acid ethyl ester.

25. The compound in accordance with claim 2, 3-(p-chlorophenyl)-2-[2-(diethylamino)ethyl]-isoindole-1-carboxylic acid ethyl ester.

26. The compound in accordance with claim 3, 5-chloro-2-[2-(diethylamino)ethyl]-3-phenylisoindole-1-carboxylic acid methylamide.

27. The compound in accordance with claim 2, 2-[3-(butylmethylamino)propyl]-5-chloro-3-phenylisoindole-1-carboxylic acid ethyl ester.

28. The compound in accordance with claim 2, 2-{3-[bis(2-hydroxyethyl)amino]propyl}-5-chloro-3-phenylisoindole-1-carboxylic acid ethyl ester.

29. The compound in accordance with claim 3, 5-chloro-2-[2-(diethylamino)ethyl]-3-phenylisoindole-1-carboxylic acid dimethylamide.

30. The compound in accordance with claim 2, 5-chloro-3-(3,4-dichlorophenyl)-2-[2-(diethylamino)-ethyl]-isoindole-1-carboxylic acid ethyl ester.

31. The compound in accordance with claim 2, 2-[2-(diethylamino)ethyl]-3-phenyl-5-trifluoromethyl-isoindole-1-carboxylic acid ethyl ester.

32. The compound in accordance with claim 3, 5-chloro-2-[2-(diethylamino)ethyl]-3-phenylisoindole-1-carboxylic acid ethylamide.

33. The compound in accordance with claim 2, 2-[5-(butylmethylamino)-3,3-dimethylpentyl]-5-chloro-3-phenylisoindole-1-carboxylic acid ethyl ester.

34. The compound in accordance with claim 2, 5-chloro-2-[4-(isopropylamino)pentyl]-3-phenylisoindole-1-carboxylic acid ethyl ester.

35. The compound in accordance with claim 2, 5-chloro-2-{3-[bis(methoxyethyl)amino]propyl}-3-phenylisonindole-1-carboxylic acid ethyl ester.

36. The compound in accordance with claim 2, 2-[3-(cyclohexylamino)propyl]-5-chloro-3-phenylisoindole-1-carboxylic acid ethyl ester.

37. The compound in accordance with claim 2, 5-chloro-2-[3-(N-methylanilino)propyl]-3-phenylisoindole-1-carboxylic acid ethyl ester.

38. A composition comprising a compound of the formula wherein A is alkylene containing 2–10 carbon atoms, Z is the group —OR or $$-N\begin{matrix}R_7\\R_8\end{matrix},$$

R is alkyl, cycloalkyl, cycloalkylalkyl, alkoxyalkyl, allyl or aralkyl, R$_1$, R$_2$, R$_3$ and R$_4$, independently, are hydrogen, halogen, alkyl, alkoxy or trifluoromethyl, and R$_5$ and R$_6$, independently, are hydrogen, alkyl, cycloalkyl, cycloalkylalkyl, hydroxyalkyl, alkoxyalkyl, aryl or aralkyl, or R$_5$ and R$_6$, taken together, are the group —(CH$_2$)$_n$—, wherein n is an integer of 2–7, or R$_5$ and R$_6$, taken together with the nitrogen atom to which they are attached, are a 5-membered or 6-membered heterocyclic ring containing an oxygen atom or an additional nitrogen atom which may be substituted by alkyl or hydroxyalkyl, and R$_7$ and R$_8$, independently, are hydrogen, alkyl, cycloalkyl, cycloalkylalkyl, alkoxyalkyl or aralkyl, provided that at least one of R$_7$ and R$_8$ is other than hydrogen, or a pharmaceutically acceptable acid addition salt thereof, and a compatible pharmaceutical carrier material.

* * * * *

UNITED STATES PATENT AND TRADEMARK OFFICE
CERTIFICATE OF CORRECTION

PATENT NO. : 3,996,374

DATED : December 7, 1976

INVENTOR(S) : Roland Jaunin

It is certified that error appears in the above-identified patent and that said Letters Patent are hereby corrected as shown below:

Column 42, claim 1, line 38, "8-membered" should be:

6-membered

Signed and Sealed this

Sixth Day of September 1977

[SEAL]

Attest:

RUTH C. MASON
Attesting Officer

LUTRELLE F. PARKER
Acting Commissioner of Patents and Trademarks